United States Patent [19]

Breakefield et al.

[11] Patent Number: 5,965,441
[45] Date of Patent: Oct. 12, 1999

[54] HSV/AAV HYBRID AMPLICON VECTORS

[75] Inventors: Xandra O. Breakefield, Newton; David R. Jacoby, Boston; Frances I. Smith, Lincoln, all of Mass.

[73] Assignee: The General Hospital Coporation, Boston, Mass.

[21] Appl. No.: 08/968,434

[22] Filed: Nov. 12, 1997

Related U.S. Application Data

[60] Provisional application No. 60/030,694, Nov. 13, 1996.

[51] Int. Cl.$^6$ ............... C12N 15/63; C12N 15/00; A01N 43/04; A61K 31/70
[52] U.S. Cl. ............... 435/456; 435/320.1; 435/457; 435/69.1; 435/325; 514/44; 424/93.21
[58] Field of Search ............... 435/456, 320.1, 435/457, 69.1, 325; 514/44; 424/93.21

[56] References Cited

U.S. PATENT DOCUMENTS

| | | |
|---|---|---|
| 5,254,342 | 10/1993 | Shen et al. ............... 424/401 |
| 5,354,844 | 10/1994 | Beug et al. ............... 530/345 |
| 5,521,291 | 5/1996 | Curiel et al. ............... 530/391.7 |
| 5,547,932 | 8/1996 | Curiel et al. ............... 435/65 |
| 5,635,380 | 6/1997 | Naftilan et al. ............... 435/172.3 |
| 5,646,034 | 7/1997 | Mamounes et al. ............... 435/325 |

FOREIGN PATENT DOCUMENTS

| | | |
|---|---|---|
| WO 91/16024 | 10/1991 | WIPO . |
| WO 94/06922 | 3/1994 | WIPO . |
| WO 95/06743 | 3/1995 | WIPO . |

OTHER PUBLICATIONS

Bett, A.J., et al., "An efficient and flexible system for construction of adenovirus vectors with insertions or deletions in early regions 1 and 3," *Proc. Natl. Acad. Sci USA* 91:8802–8806 (1994).

Borghesani, P.R., et al., "Genetic Methods for Increasing the Viability of Fetal Mesencephalic Neurons In Vitro and In Vivo," *Society for Neuroscience Abstracts* 21:2026 (Abstract No. 796.6) (Nov. 1995.).

Cotten, M., et al., "High–efficiency receptor–mediated delivery of small and large (48 kilobase gene constructs using the endosome–disruption activity of defective or chemically inactivated adenovirus particles," *Proc. Natl. Acad. Sci USA* 89:6094–6098 (1992).

Emi, N., et al., "Pseudotype Formation of Murine Leukemia Virus with the G Protein of Vesicular Stomatitis Virus," *J. Virol.* 65(3):1202–1207 (1991).

Friedmann, T., "Gene therapy for neurological disorders," *Trends in Genetics* 10: 210–214 (1994).

Janik, J.E., et al., "Efficient Synthesis of Adeno–Associated Virus Structural Proteins Requires Both Adenovirus DNA Binding Protein and VA I RNA," *Virology* 168:320–329 (1989).

Johnston, K.M., et al., "HSV/AAV Hybrid Amplicon Vectors Extend Transgene Expression in Human Glioma Cells," *Hum. Gene Ther.* 8(3):359–370 (Feb. 1997).

Jolly, D., "Viral vector systems for gene therapy," *Cancer Gene Therapy* 1(1):51–64 (1994).

Kennedy, P.G.E., "Potential use of herpes simplex virus (HSV) vectors for gene therapy of neurological disorders," *Brain* 120:1245–1259 ( Jul. 1997).

Landau, N.R. and D.R. Littman, "Packaging System for Rapid Production of Murine Leukemia Virus Vectors with Variable Tropism," *J. Virology* 66(8):5110–5113 (1992).

Michael, S.I. and D.T. Curiel, "Strategies to achieve targeted gene delivery via the receptor–mediated endocytosis pathway," *Gene Ther.* 1:223–232 (1994).

Miller, A.D., et al., "Factors Involved in Production of helper Virus–Free Retrovirus Vectors," *Somatic Cell Mol. Gen* 12(2): 175–183 (1986).

Mitani, K., et al., "Rescue, propagation, and partial purification of a helper virus–dependent adenovirus vector," *Proc. Natl. Acad. Sci. USA* 92:3854–3858 (Apr. 1995).

Mulligan, R.C., "The Basic Science of Gene Therapy," *Science* 260:926–932 (1993).

Muzyczka, N., "Use of Adeno–Associated Virus as a General Transduction Vector for Mammalian Cells," *Curr. Topics Microbiol. Immunol.* 158:97–129 (1992).

Naldini, L., et al., "In Vivo Gene Delivery and Stable Transduction of Nondividing Cells by a Lentiviral Vector," *Science* 272:263–267 (Apr. 1996).

Orkin, S.H. and A.G. Motulsky, "Report and Recommendations of the Panel to Assess the NIH Investment in Research on Gene Therapy," pp. 1–40 (Dec. 1995).

Samulski, R.J., "Adeno–associated virus: integration at a specific chromosomal locus," *Curr. Opin. Genet. Dev.* 3:74–80 (1993).

Smith, F., et al., "Virus vectors for gene delivery to the nervous system," *Rest. Neurol. Neurosci.* 8: 21–34 (Jun. 1995).

Strair, R.K., et al., "Retroviral mediated gene transfer into bone marrow progenitor cells: use of beta–galactosidase as a selectable marker," *Nucleic Acids Res.* 18(16):4759–4762 (1990).

von Rüden, T., et al., "Generation of High–Titer Retroviral Vectors Following Receptor–Mediated, Adenovirus–Augmented Transfection," *Biotechniques* 18(3):484–489 (Mar. 1995).

(List continued on next page.)

*Primary Examiner*—Deborah Crouch
*Assistant Examiner*—Jill D. Martin
*Attorney, Agent, or Firm*—Sterne, Kessler, Goldstein & Fox P.L.L.C.

[57] ABSTRACT

The present invention relates to a hybrid vector system which incorporates elements of herpesvirus and adeno-associated virus and which is capable of expressing a gene product in eukaryotic cells. The vector system of the present invention provides a means of packaging plasmid DNA into highly infectious virions which can efficiently and safely deliver large transgenes to both mitotic and postmitotic cells in a state which can be maintained for extended periods. The invention pertains to the use of this vector system in introducing and expressing gene sequences in mitotic and postmitotic cells.

10 Claims, 8 Drawing Sheets

OTHER PUBLICATIONS

Wagner, E., et al., "Coupling of Adenovirus to transferrin–polylysine/DNA complexes greatly enhances receptor–mediated gene delivery and expression of transfected genes," *Proc. Natl. Acad. Sci. USA 89*:6099–6103 (1992).

Wang, S. and J.–M. Vos, "A Hybrid Herpesvirus Infectious Vector Based on Epstein–Barr Virus and Herpes Simplex Virus Type 1 for Gene Transfer into Human Cells In Vitro and In Vivo," *J. Virol. 70(12)*:8422–8430 (Dec. 1996).

Webster, A., et al., "The Adenovirus Protease is Activated by a Virus–Coded Disulphide–Linked Peptide," *Cell 72*:97–104 (1993).

HSV/AAV HYBRID AMPLICON VECTORS

PRIOR APPLICATION INFORMATION

This application claims the benefit of the filing date of provisional application 60/030,694 filed on Nov. 13, 1996, which is herein incorporated by reference.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The present invention relates to a hybrid vector system which incorporates elements of herpesvirus and adeno-associated virus and which is capable of expressing a gene product in eukaryotic cells. The vector system of the present invention provides a means of packaging plasmid DNA into highly infectious virions which can efficiently and safely deliver large transgenes to both mitotic and postmitotic cells in a state which can be maintained for extended periods. The invention also pertains to the use of this vector system in introducing and expressing gene sequences in mitotic and postmitotic cells for therapeutic purposes.

2. Related Art

A variety of vectors have been developed for gene delivery to the nervous system and to brain tumors. These vectors derive from herpes simplex virus type 1 (HSV-1), adenovirus, adeno-associated virus (AAV) and retrovirus constructs (for review see Friedmann, T., *Trends Genet* 10:210–214 (1994); Jolly, D., *Cancer Gene Therapy* 1 (1994); Mulligan, R. C., *Science* 260:926–932 (1993); Smith, F. et al., *Rest. Neurol. Neurosci.* 8:21–34 (1995)). Vectors based on HSV-1, including both recombinant virus vectors and amplicon vectors, as well as adenovirus vectors can assume an extrachromosomal state in the cell nucleus and mediate limited, long term gene expression in postmitotic cells, but not in mitotic cells. HSV-1 amplicon vectors can be grown to relatively high titers ($10^7$ transducing units/ml) and have the capacity to accommodate large fragments of foreign DNA (at least 15 kb, with 10 concatemeric copies per virion). AAV vectors (rAAV), available in comparable titers to amplicon vectors, can deliver genes (<4.5 kb) to postmitotic, as well as mitotic cells in combination with adenovirus or herpes virus as helper virus. Long term transgene expression is achieved by replication and formation of "episomal" elements and/or through integration into the host cell genome at random or specific sites (for review see Samulski, R. J., *Current Opinion in Genetics and Development* 3:74–80 (1993); Muzyczka, N., *Curr. Top. Microbiol. Immunol.* 158:97–129 (1992)). HSV, adenovirus and rAAV vectors are all packaged in stable particles. Retrovirus vectors can accommodate 7–8 kb of foreign DNA and integrate into the host cell genome, but only in mitotic cells, and particles are relatively unstable with low titers. Recent studies have demonstrated that elements from different viruses can be combined to increase the delivery capacity of vectors. For example, incorporation of elements of the HIV virion, including the matrix protein and integrase, into retrovirus vectors allows transgene cassettes to enter the nucleus of non-mitotic, as well as mitotic cells and potentially to integrate into the genome of these cells (Naldini, L. et al., *Science* 272:263–267 (1996)); and inclusion of the vesicular somatitis virus envelope glycoprotein (VSV-G) increases stability of retrovirus particles (Emi, N. et al., *J. Virol.* 65:1202–1207 (1991)). As another example, inclusion of elements from Epstein Barr virus (EBV)—the DNA origin of replication, oriP, and the EBNA-1, within HSV amplicon vectors allows nuclear replication of vectors in dividing human cells (Wang and Vos, in press). Still there is a need for a safe, high titer vector with a broad host range which has a large transgene capacity and can confer stable expression in both mitotic and non-mitotic cells.

SUMMARY OF THE INVENTION

According to the invention there is provided a hybrid gene vector capable of expressing a gene sequence comprising a nucleic acid in which a polynucleotide sequence to be carried by the vector into a target cell, such as a gene sequence or transgene, is fused (i) to a subset of viral polynucleotide sequences from a herpesvirus comprising a herpesviral origin of replication and packaging signal sufficient for replication and packaging of the vector in herpesviral virions, and (ii) to a subset of viral polynucleotide sequences from an adeno-associated virus (AAV) comprising AAV elements sufficient to increase persistence of the vector in mitotic and non-mitotic cells.

Preferably the hybrid gene vector also comprises an adeno-associated viral gene(s) and a suitable arrangement of AAV polynucleotide elements, sufficient for replication and chromosomal integration of the polynucleotide sequence that is to be carried by the vector into the target cell.

For example, the polynucleotide sequence to be carried by the vector into the target cell can be arranged between AAV ITR terminal repeats, and the adeno-associated viral gene can be a Rep gene encoding Rep enzyme(s) capable of mediating replication and chromosomal integration of ITR-flanked polynucleotide sequences.

In certain embodiments, the AAV elements can also be suitably arranged for and sufficient to enable sufficient replication and packaging the vector in AAV virions.

The vector, when encapsulated in either a herpesviral particle coat or an adeno-associated viral particle coat, is capable of binding to a target host cell and introducing into the target host cell the polynucleotide sequence carried by the vector.

The present invention further relates to a hybrid vector system which incorporates elements of HSV amplicon vectors and rAAV vectors. HSV amplicon elements comprise the origin of DNA replication, $ori_S$, and the virion packaging signal, pac. AAV elements comprise the terminal repeats, ITRs, which are sufficient for replication and packaging of AAV virions, and the rep gene, which encodes Rep isozymes involved in replication and chromosomal integration of ITR-flanked sequences. The vector system is capable of infecting and persisting in mitotic and non-mitotic cells and can be used in gene therapy to treat diseases and disorders including brain tumors.

The invention also provides a hybrid vector capable of expressing a transgene comprising:

(a) a DNA sequence derived from Herpes Simplex Virus (HSV) comprising a HSV origin of DNA replication and packaging signal; and (b) inverted terminal repeat sequences from Adeno-Associated Virus (AAV) flanking a transgene cassette.

The invention also provides a hybrid vector capable of expressing a transgene comprising:

(a) a DNA sequence derived from Herpes Simplex Virus (HSV) comprising a HSV origin of DNA replication and packaging signal;

(b) inverted terminal repeat sequences from Adeno-Associated Virus (AAV) flanking a transgene cassette; and (c) an AAV rep gene inserted outside the inverted terminal repeat flanked transgene cassette.

The vector system of the present invention is designed to provide a means of packaging plasmid DNA into highly infectious virions which can efficiently and safely deliver large transgenes to both mitotic and postmitotic cells in a state which can be maintained for extended periods.

The invention further concerns the above-described recombinant vectors which are pHS/AVrep$^+$ and pHS/AVrep$^-$.

The invention also provides the above-described recombinant vector that can be used in any therapeutic modality wherein the inserted transgene sequence is a gene sequence associated with diseases and disorders including but not limited to inherited metabolic disorders, including, lysosomal storage disease, Lesch-Nyhan syndrome, inherited neurological diseases, including, amyloid polyneuropathy, Alzheimer's Disease, Duchenne's muscular dystrophy, ALS, Parkinson's Disease and brain tumors, diseases of the blood, such as, sickle-cell anemia, clotting disorders and thalassemias, cystic fibrosis, diabetes, disorders of the liver and lung, heart and vascular disease, diseases associated with hormone deficiencies, movement disorders, pain, stroke, and HIV.

The invention further provides a method for expressing a transgene in a cell. The invention also provides a method of treating diseases and disorders. In addition, the invention provides a method of selectively killing tumor cells.

Non-limiting examples of the diseases and disorders that can be treated using the present hybrid vectors includes: inherited metabolic disorders, including, lysosomal storage disease, Lesch-Nyhan syndrome, inherited neurological diseases, including, amyloid polyneuropathy, Alzheimer's Disease, Duchenne's muscular dystrophy, ALS, Parkinson's Disease, diseases of the blood, such as, sickle-cell anemia, clotting disorders and thalassemias, cystic fibrosis, diabetes, disorders of the liver and lung, heart and vascular disease, diseases associated with hormone deficiencies, movement disorders, pain, stroke, HIV, tumors, neoplasms, carcinomas, sarcomas, leukemias, lymphoma, astrocytomas, oligodendrogliomas, meningiomas, neurofibromas, ependymomas, Schwannomas, neurofibrosarcomas, and glioblastomas.

Cells were maintained in active cell growth by splitting in a 1:4 ratio every 5 days. At the time points indicated, parallel culture were stained for lacZ (Panel A) or evaluated for viable cell number (Panel B). (Results are shown as the mean±standard error of the mean from two experiments).

Figure 3A:
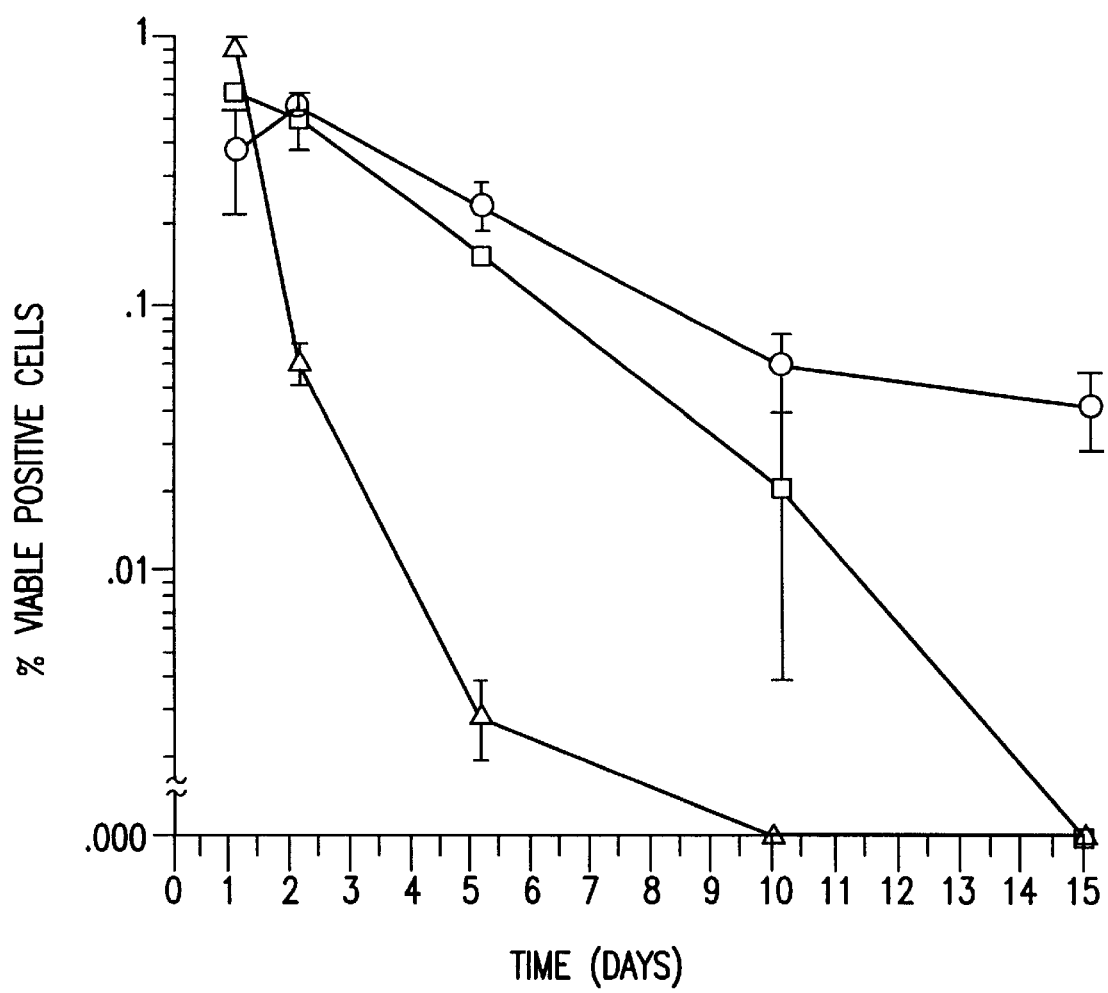
FIGS. 3A–B. Transduction of glioma cells using amplicon vectors with helper virus. Proliferating U87 human glioma cells in culture ($2 \times 10^5$ cells/well) were infected with amplicon vector stocks on day 0 at an MOI of 0.05 transducing units per cell or with a ICP27-minus helper virus alone at an MOI of 16 pfu/cell. HS/AAVrep$^+$(open circle); HS/AAVrep$^-$(open square); Hermes-L (triangle), HSV helper virus (filled square) and uninfected U87 cells (filled circle).
Figure 3B:
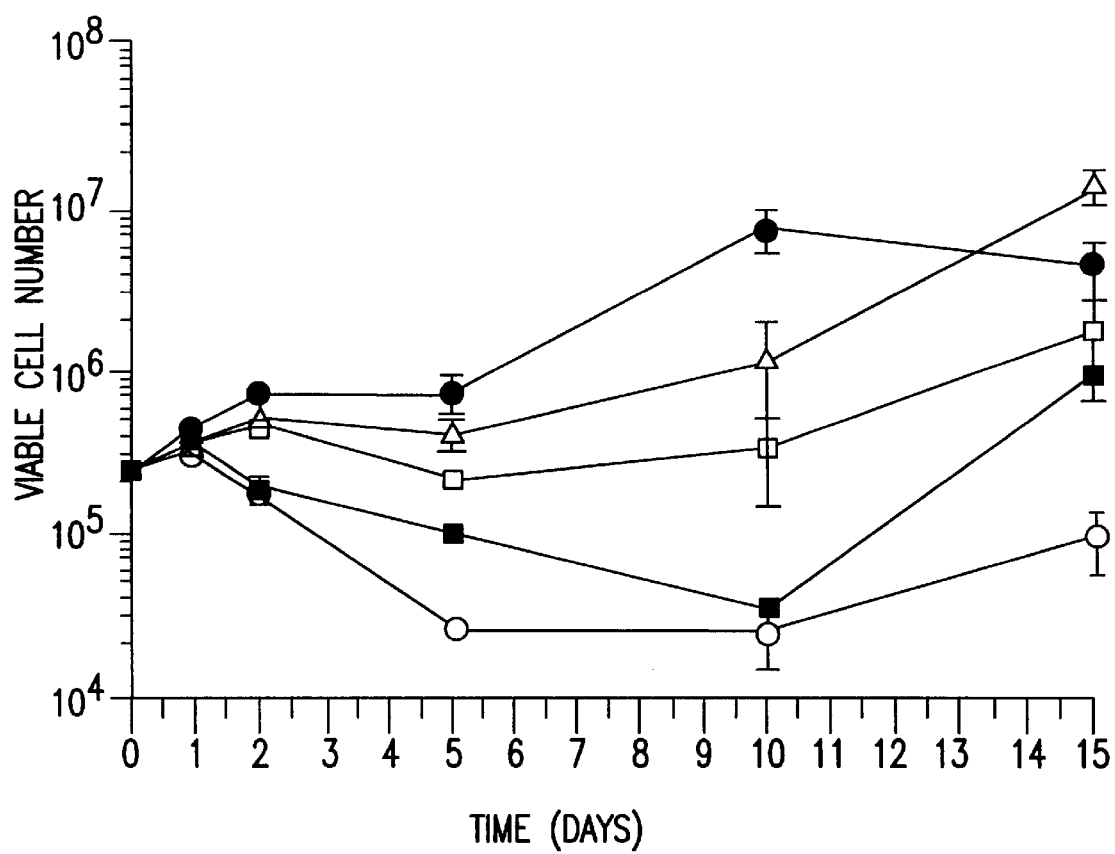
Figure 4A:
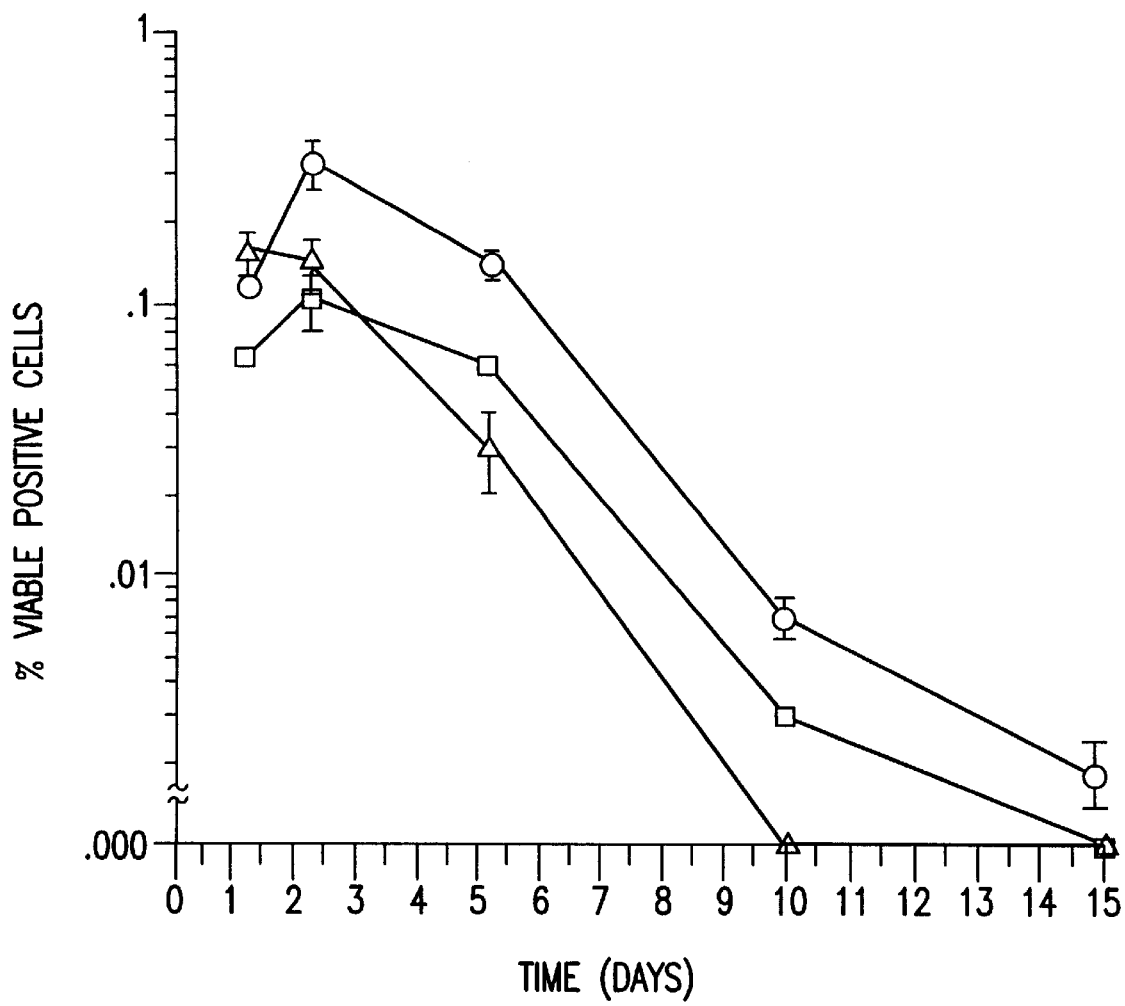
Figure 4B:
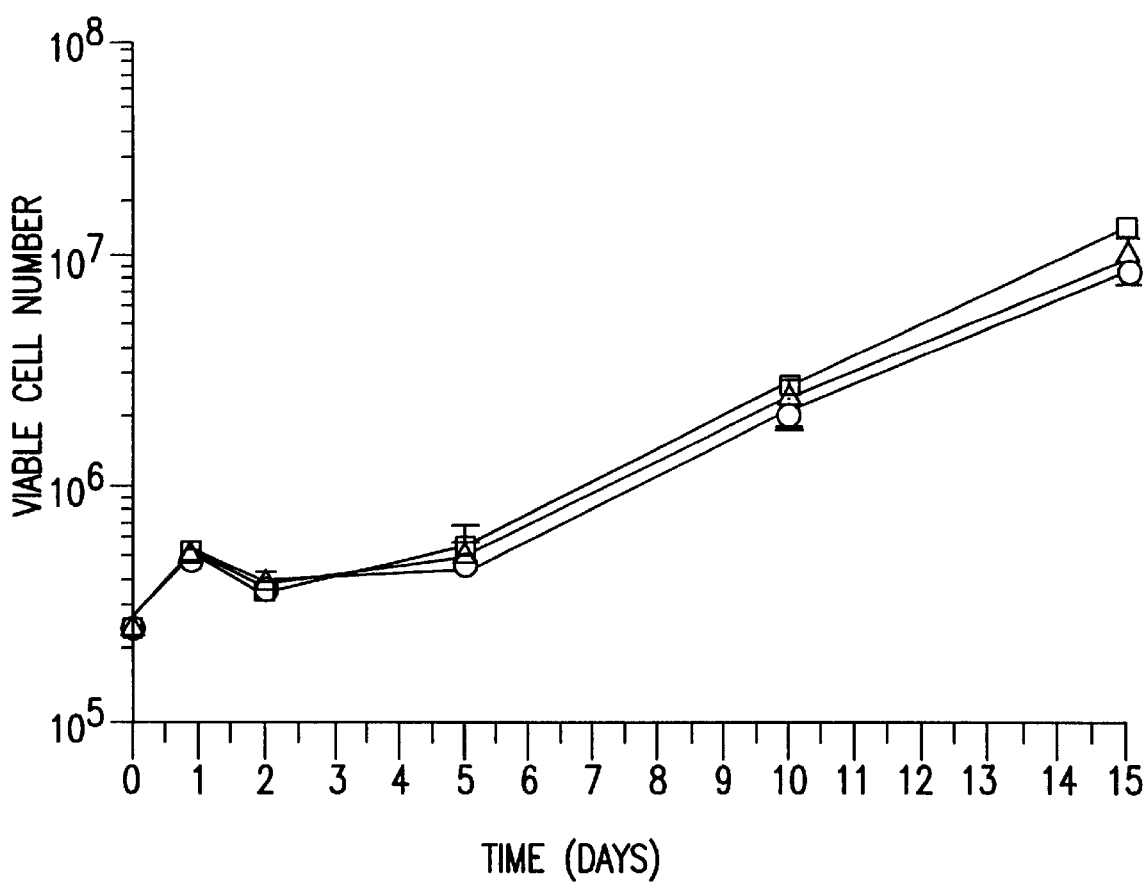

FIGS. 4A–B. Transduction of glioma cells using helper virus-free amplicon vectors. The experiment was carried out as in FIG. 3A–B except helper-free amplicon vector stocks were used.

Figure 5:
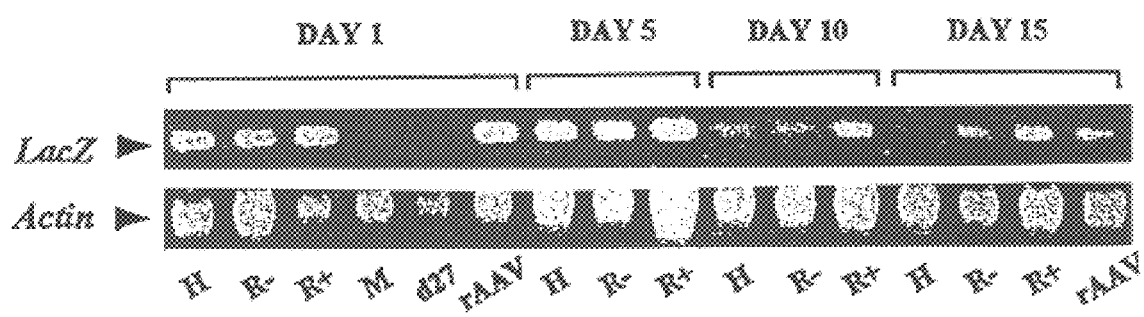

FIG. 5. PCR analyses of DNA in infected cells. Cells were transduced with helper-free amplicon vectors and analyzed as described in FIG. 3. On days 1, 5, 10 and 15 post-transduction cells were harvested and total cellular DNA was used for PCR using either lacZ primers or β-actin primers. Cells were transduced with: H=Hermes-L, R$^-$=HS/AVrep$^-$, R$^+$=HS/AVrep$^+$ or M=were not transduced.

Figure 6:
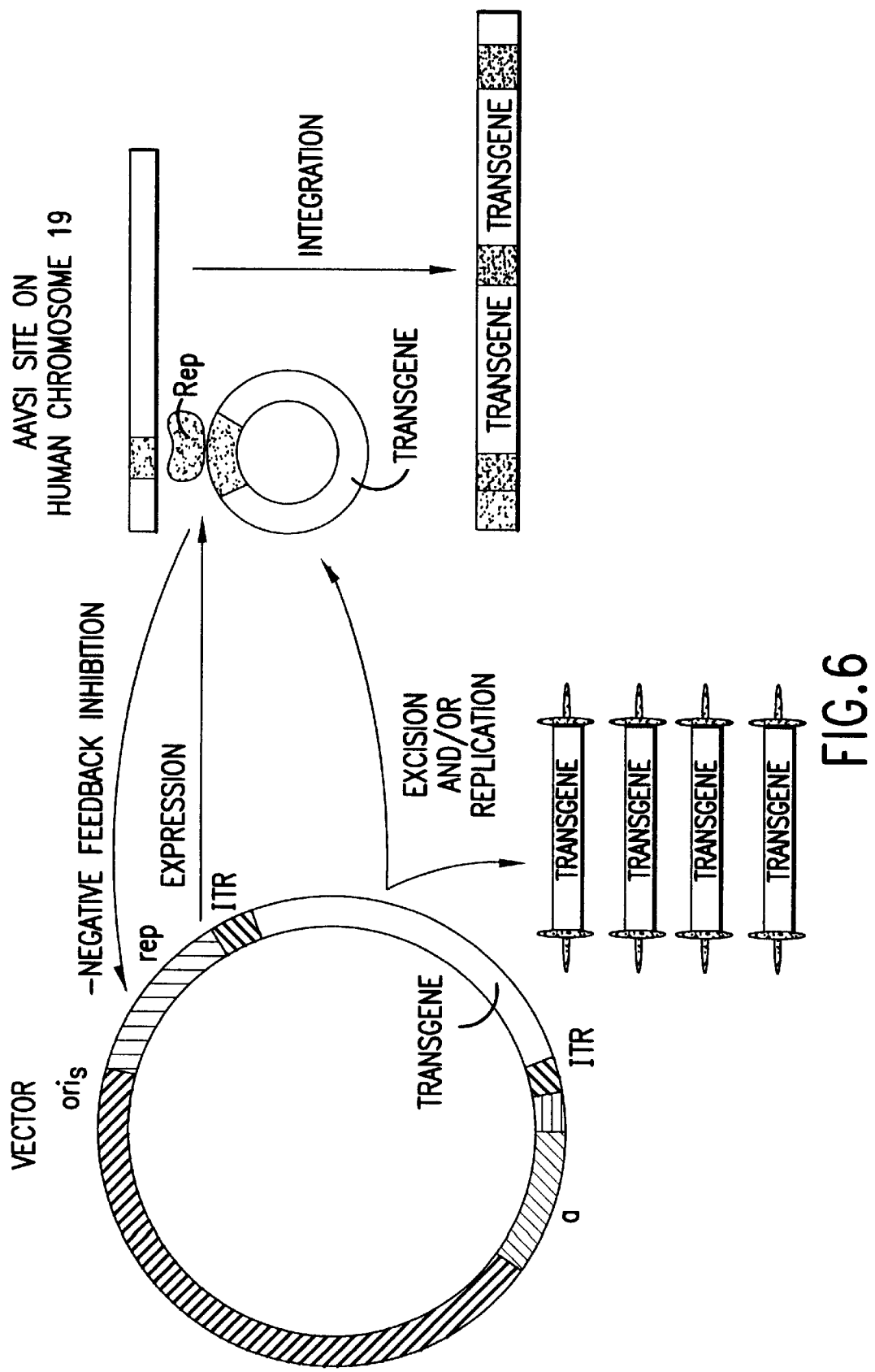

FIG. 6. Mechanisms for extended transgene expression by the hybrid vector. The inventors propose the following mechanism: the hybrid vector enters the host cell nucleus as a linear double stranded DNA concatenate. The transgene can be replicated out of the amplicon backbone thereby amplifying the transgene cassette and stabilizing it through hairpin hybridization of the AAV ITR sequences. Alternatively, it can integrate into the host cell genome. In the presence of Rep in human cells this should preferentially occur at the AAVS1 site on chromosome 19, but can also occur at random chromosomal sites in the presence or absence of Rep in different species.

DETAILED DESCRIPTION OF THE PREFERRED EMBODIMENTS

The vector system of the present invention provides a means of packaging plasmid DNA into highly infectious virions which can efficiently and safely deliver large transgenes to both mitotic and postmitotic cells in a state which can be maintained for extended periods. The HSV/AAV hybrid vectors of the present invention combine the advantages of two gene delivery vehicles, namely HSV-1 amplicons and recombinant (r) AAV vectors. Hybrid vectors bear the oriS and pac features of HSV amplicons and a transgene cassette flanked by AAV ITR sequences, with or without the AAV rep gene outside the cassette.

Herpes Simplex Virus-1 and Adeno-associated Virus

HSV-1 is a double-stranded DNA virus which is replicated and transcribed in the nucleus of the cell. HSV-1 has both a lytic and a latent cycle. HSV-1 has a wide host range, and infects many cell types in mammals and birds (including chicken, rat, mice monkey, and human) Spear et al., *DNA Tumor Viruses*, J. Tooze, Ed. (Cold Spring Harbor Laboratory, Cold Spring Harbor, N.Y., 1981) pp. 615–746.

HSV-1 can lytically infect a wide variety of cells including neurons, fibroblasts and macrophages. In addition, HSV-1 infects post-mitotic neurons in adult animals and can be maintained indefinitely in a latent state. Stevens, *Current Topics in Microbiology and Immunology* 70: 31(1975). Latent HSV-1 is capable of expressing genes.

AAV also has a broad host range and until recently, all human cells were thought to be infectable. However, Ponnazhagan and co-workers have identified that human megakaryocytic leukemia cells are non-permissive for AAV infection. The host range for integration is believed to be equally broad. AAV is a single stranded DNA parvovirus endogenous to the human population, making it a suitable gene therapy vector candidate. AAV is not associated with any disease, therefore making it safe for gene transfer applications (Cukor et al., The Parvoviruses, Ed. K. I. Bems, Plenum, N.Y., (1984) pp. 33–36; Ostrove et al., Virology 113: 521 (1981)). AAV integrates into the host genome upon infection so that transgenes can be expressed indefinitely (Kotin et al., Proc. Natl. Acad. Sci. USA 87: 221 (1990); Samulski et al., Embo J. 10: 3941 (1991)). Integration of AAV into the cellular genome is independent of cell replication which is particularly important since AAV can thus transfer genes into quiescent cells (Lebkowski et al., Mol. Cell. Biol. 8:3988 (1988)).

Vectors based on HSV-1, including both recombinant virus vectors and amplicon vectors, as well as adenovirus vectors can assume an extrachromosomal state in the cell nucleus and mediate limited, long term gene expression in postmitotic cells, but not in mitotic cells. HSV-1 amplicon vectors can be grown to relatively high titers ($10^7$ transducing units/ml) and have the capacity to accommodate large fragments of foreign DNA (at least 15 kb, with 10 concatemeric copies per virion). AAV vectors (rAAV), available in comparable titers to amplicon vectors, can deliver genes (<4.5 kb) to postmitotic, as well as mitotic cells.

The components of the hybrid vector system of the present invention have many intriguing features derived from their parent viruses. Both HSV and AAV can deliver genes to dividing and non-dividing cells. In general, HSV virions are considered more highly infectious that AAV virions, with a ratio of virus particles: infectious units in the range of 10 for HSV (Browne, H. et al., *J Virol.* 70:4311–4316 (1996)) and up to thousands for AAV (Snyder, R. O. et al., In Current Protocols in Human Genetics, Eds. Dracopoli, N. et al., John Wiley and Sons: New York (1996), pp. 1–24), and both having a broad species range. Still, each virion has specific trophisms which will affect the efficiency of infection of specific cell types. The recent identification of a membrane receptor for HSV-1 which is a member of the tumor necrosis factor alpha family (Montgomery, R. I. et al., 21st Herpes Virus Workshop Abstract #167 (1996)) indicates that the distribution of this receptor will affect the relative infectibility of cells, albeit most mammalian cell types appear to be infectible with HSV-1. AAV also has a very wide host and cell type range. The cellular receptor for AAV is not known, but a 150 kDA glycoprotein has been described whose presence in cultured cells correlates with their ability to bind AAV (Mizukami, H. et al., *Virology* 217:124–130 (1996)).

The Hybrid Vectors of the Present Invention

The present invention provides for HSV/AAV hybrid vectors that were designed to combine advantages of both HSV-1 amplicon vectors and rAAV vectors. The "backbone" of one embodiment of the vector of the present invention is an HSV-1 amplicon consisting of a plasmid containing two non-coding elements of HSV-1, the origin of DNA replication, oris, and the DNA cleavage/packaging signal, pac, which allow replication and packaging of DNA as a concatenate in HSV-1 virions in the presence of HSV-1 helper virus (Kwong, A. D. and Frenkel, N., *In Viral Vectors*, Eds. M. G, Kaplitt and A. D. Loewy, Academic Press: New York (1995), pp. 25–42). Within this amplicon "backbone" elements of rAAV vectors were introduced. rAAV vectors contain, at minimum, the inverted terminal repeat elements (ITR's) flanking a transgene cassette; they are packaged into AAV virions by cotransfection of cells with a plasmid bearing the AAV rep and cap genes, which encode proteins that mediate replication and genomic integration of AAV sequence, as well as packaging and formation of AAV virions, respectively, and infection with a defective helper virus, either adenovirus or HSV-1 (Samulski, R. J., *Current Opinion in Genetics and Development* 3:74–80 (1993); Muzyczka, N., *Curr. Top. Microbiol. Immunol.* 158:97–129 (1992)). rAAV vectors without the rep gene appear to replicate and integrate at random sites in the host cell genome, while expression of Rep proteins Rep 68 and Rep 78, can mediate genomic integration into a well-defined locus on human chromosome 19 (Kotin, R. M. et al., *Proc. Natl. Acad. Sci. USA* 87:2211–2215 (1990); Samulski, R. J. et al., *EMBO J* 10:3941–3950 (1991); Giraud, C. et al., *Proc. Natl. Acad. Sci. USA* 91:10039–10043 (1994); Weitzman, M. D. et al., *Proc. Natl. Acad. Sci. USA* 91:5808–5812 (1994)). In the hybrid vector of the present invention, the transgene cassette is flanked by the AAV ITR sequences in order to promote replicative amplification in the host cell nucleus and integration into the host cell genome.

Such amplified transgene cassettes have been reported to form stable hairpin ends, which resist exonuclease digestion (Bohenzky, R. A. and Bems, K. I., *J Mol. Biol.* 206:91–100 (1989)). In the rep$^+$ hybrid vector the AAV rep gene is placed outside of the expression cassette so that it will not be amplified or be integrated into the cellular genome. By placing the rep gene under its own promoter it should also be subject to feed-back inhibition of expression, thus reducing the toxic effects of Rep proteins (Labow, M. A. et al., *J Virol.* 60:251–258 (1986)). At the same time limited expression of Rep 68 and Rep 78 is available to direct site specific integration of the transgene cassette into the AAVS1 locus on human chromosome 19.

According to the invention there is provided a hybrid gene vector capable of expressing a gene sequence comprising a nucleic acid in which a polynucleotide sequence to be carried by the vector into a target cell, such as a gene sequence or transgene, is fused (i) to a subset of viral polynucleotide sequences from a herpesvirus comprising a herpesviral origin of replication and packaging signal sufficient for replication and packaging of the vector in herpesviral virions, and (ii) to a subset of viral polynucleotide sequences from an adeno-associated virus (AAV) comprising AAV elements sufficient to increase persistence of the vector in mitotic and non-mitotic cells.

Preferably the hybrid gene vector also comprises an adeno-associated viral gene(s) and a suitable arrangement of AAV polynucleotide elements, sufficient for replication and chromosomal integration of the polynucleotide sequence that is to be carried by the vector into the target cell.

For example, the polynucleotide sequence to be carried by the vector into the target cell can be arranged between AAV ITR terminal repeats, and the adeno-associated viral gene can be a Rep gene encoding Rep enzyme(s) capable of mediating replication and chromosomal integration of ITR-flanked polynucleotide sequences.

In certain embodiments, the AAV elements can also be sufficient to enable sufficient and suitably arranged for replication and packaging the vector in AAV virions.

The vector, when encapsulated in either a herpesviral particle coat or an adeno-associated viral particle coat, is capable of binding to a target host cell and introducing into the target host cell the polynucleotide sequence carried by the vector.

The hybrid vectors of the present invention will preferably contain:

(1) a sequence which contains an HSV-1 packaging site, pac (preferably the HSV-1 segment located in the A repeat element of HSV-1 virus, or its equivalent) (Davidson, A. J., et al. *J Gen. Virol.* 55:315 (1981), such that the vector can be packaged into a particle which is capable of adsorbing to a cell;

(2) a sequence which contains an HSV-1 origin of DNA replication (preferably the HSV-1 c region, containing the HSV-1 $ori_S$ region, located in the repeat element of the S component of HSV-1 virus, or its equivalent) (McGeoch, D. J., et al., Nucleic Acids Res. 14:1727 (1986));

(3) a transgene cassette flanked by AAV ITR sequences (preferably the AAV ITR region located in the terminal 145 bp of the AAV genome (at approximately nucleotides 1–145 of AAV) or its equivalent.

An even more preferred vector of the present invention will, in addition to the above-enumerated sequences (1), (2) and (3), contain the following sequence:

(4) a AAV rep gene sequence (preferably the AAV Rep gene encoding all four rep isozymes) inserted outside the ITR sequence flanked transgene cassette. The rep gene may be operably linked to its own promoter or any other suitable eukaryotic promoter known in the art.

Thus, the vectors of the present invention will preferably contain the $ori_S$ and pac features of HSV amplicons and a transgene cassette flanked by AAV ITR sequences, with or without the AAV rep gene outside the transgene cassette.

Figure 1:
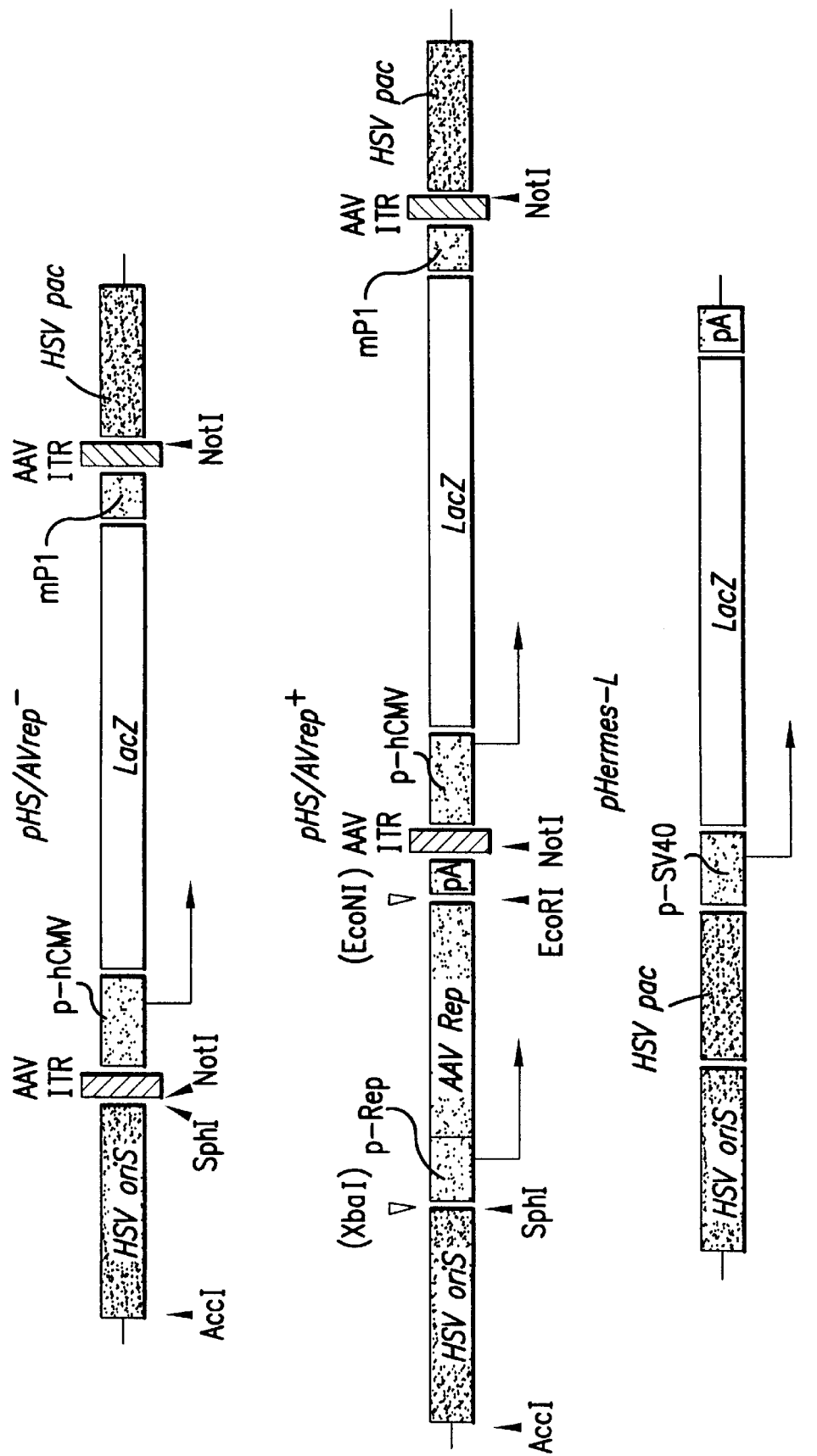
FIG. 1. Amplicon constructs. Transgene elements bearing the marker lacZ gene were introduced into conventional amplicon vectors bearing the HSV-1 origin of DNA replication, oriS, and DNA cleavage/packaging signal, pac, with and without additional AAV elements. In hybrid plasmids pHS/AVrep$^-$ and pHS/AVrep$^+$ the transgene cassette comprises lacZ under control of the human CMV IEI promoter (p–) and terminated with a splice junction and polyadenylation signal (MI) and flanked with AAV ITRs. pHS/AVrep$^+$ contains in addition the wild type AAV rep gene under its own promoters (p-Rep). In the conventional amplicon pHermes-L lacZ is under control of the SV40 promoter and terminated with an SV40 polyadenylation signal.

Structural and genetic characteristics of the hybrid vectors of the present invention can be most clearly illustrated by a description of the most preferred hybrid vectors, pHA/AVrep$^-$ and pHA/AVrep$^+$. These vectors are depicted in FIG. 1. The present vectors were constructed as follows.

Briefly, plasmids pAB-11 (Goodman, S. et al., *Blood* 84:1492–1500 (1994)), psub201 (Samulski, R. J. et al., *J Virol.* 63:3822–3825 (1989)), and pAAV/Ad 8 (Samulski, R. J. et al., *J Virol.* 63:3822–3825 (1989)). pAB 11 contains a transgene cassette13 including the *E. coli* lacZ gene, modified to encode a nuclear localization signal, under control of the CMV immediate early (IE) 1 promoter and followed by the mouse protamine 1 (mP1) splice site and polyadenylation signal, all flanked by the AAV ITRs (Goodman, S. et al., *Blood* 84:1492–1500 (1994)). psub201 is an infectious AAV cDNA with 45 bp deletions in the ITR and intact rep and cap genes. pAAV/Ad8 contains the wild type AAV rep and cap genes flanked by the adenovirus type 5 terminal sequences (107 bp) in place of the AAV ITRs (Samulski, R. J. et al., *J Virol.* 63:3822–3825 (1989)). The amplicon plasmid, pHSH4.6 contains the HSV-1 origin of DNA replication, $ori_S$, and DNA cleavage/packaging signal, pac, as well as the *E. coli* origin of DNA replication (ori) and ampicillin resistance (amp$^r$) gene, and includes a transgene cassette in which lacZ is under control of the SV40 promoter and followed by an SV40 polyadenylation signal (Pechan, P. A. et al., *Hum. Gene. Ther.* 7:2003–2013 (1996)). The amplicon plasmid, pHermes-L contains HSV-1 $ori_S$ and pac sequences, as well as the *E. coli* ori and amp$^r$ sequences, and bears the lacZ gene under control of the SV40 promoter and followed by the SV40 polyadenylation signal (Pechan, P. A. et al., *Hum. Gene. Ther.* 7:2003–2013 (1996)).

The AAV ITR flanked marker gene for both pHS/AVrep$^-$ and pHS.AVrep$^+$ were derived from pAB-11. The ITR flanked lacZ expression cassette was isolated by PstI digestion of pAB-11, fragment ends were subsequently made NotI compatible by addition of linkers. The amplicon parent, pHSH4.6 was modified to have a unique NotI site by inserting an adapter at the unique BamHI site. HS/AVrep$^-$ amplicons were derived by insertion of the PstI/NotI-adapted fragment of pAB-11 into the NotI site of the NotI modified pHSH4.6. HS/AVrep$^+$ amplicons were constructed by inserting an XbaI/EcoNI fragment of psub201, containing the endogenous promoters and coding sequences of all four Rep isoforms, upstream of the SV40 polyadenylation site in HS/AVrep$^-$.

A hybrid vector, as used herein, is a nucleic acid molecule (preferably DNA) in which a gene sequence, or a transgene, is fused to a subset of viral sequences from Herpes Simplex Virus (HSV) and Adeno-Associated Virus (AAV). The viral sequences and the total genome size is selected such that the vector is capable of being encapsulated in either an HSV or an AAV viral particle and thus is capable of binding to, and introducing its gene sequences into a virus-sensitive host cell. The infective properties of such a virion are, thus, the same as those containing the wild type viral genome.

The term "transgene", as used herein, is intended to refer to a gene sequence and are nucleic acid molecules. Such transgenes, or gene sequences, may be derived form a variety of sources including DNA, cDNA, synthetic DNA, RNA, or combinations thereof. Such transgenes may comprise genomic DNA which may or may not include naturally occurring introns. Moreover, such genomic DNA may be obtained in association with promoter regions or poly A sequences. The transgenes of the present invention are preferably cDNA. Genomic or cDNA may be obtained by means well known in the art. A transgene which may be any gene sequence whose expression produces a gene product that is to be expressed in a cell. The gene product may affect the physiology of the host cell. Alternatively the transgene may be a selectable marker gene or reporter gene. Examples of gene sequences that can be used as trangenes include, but are not limited to, a gene sequence associated with diseases and disorders such as inherited metabolic disorders, including, lysosomal storage disease, Lesch-Nyhan syndrome, inherited neurological diseases, including, amyloid polyneuropathy, Alzheimer's Disease, Duchenne's muscular dystrophy, ALS, Parkinson's Disease and brain tumors, diseases of the blood, such as, sickle-cell anemia, clotting disorders and thalassemias, cystic fibrosis, diabetes, disorders of the liver and lung, heart and vascular disease, diseases associated with hormone deficiencies, movement disorders, pain, stroke, HIV and cancer.

The term "transgene cassette," as used herein, is intended to refer to a transgene operably linked to a promoter or other regulatory sequence sufficient to direct transcription of the transgene. Suitable promoters include, for example, as human CMV IEI promoter or an SV40 promoter. The transgene cassette may also optionally have termination signals, processing signals, or introns. It is of course possible to use as a transgene a gene sequence that already possesses a promoter, initiation sequence, introns, processing sequence or termination sequence in the transgene cassette.

A reporter gene, as used herein, is any gene sequence which, when expressed, results in the production of a protein whose presence or activity can be easily monitored.

Examples of suitable reporter genes can include the gene for β-galactosidase, galactokinase, chloramphenicol acetlytransferase, and β-lactamase.

A selectable marker gene, as used herein, is any gene sequence capable of expressing a protein whose presence permits selective propagation of a cell which contains it. Examples of selectable markers include gene sequence capable of conferring host resistance to antibiotics (such as ampicillin, tetracycline, kanamycin, etc.), amino acid analogs, or permitting growth of bacteria on additional carbon sources or under otherwise impermissible culturing conditions.

The term "host cell" is intended to refer to any cell that can be infected with the hybrid vectors of the present invention.

The term "operably linked" is intended to describe a linkage between a gene sequence and a promoter or other regulatory or processing sequence such that the transcription of the gene sequence is capable of being directed by an operably linked promoter sequence, the translation of the gene sequence is capable of being directed by an operably linked translational regulatory sequence and the post-translational processing of the gene sequence is capable of being directed by an operably linked processing sequence.

Host range and Capacity of the Hybrid Vectors

The HSV/AAV hybrid vector constructs of the present invention allow packaging of the transgene cassette into either HSV-1 or AAV virions, although the theoretical size limitation in the AAV virion would be much smaller (~4.5 kb) than the HSV virion (~150 kb). Thus, the host range of the hybrid vectors of the present invention are extended relative to the HSV-1 or AAV based vectors. Typically amplicon plasmids have been constructed in the range of 15 kb with transgene cassettes of up to 10 kb, such that about 10 copies of the amplicon are packaged as a concatenate in an HSV virion (Ho, D. Y., *Meth. Cell. Biol.* 43:191–210 (1994)).

Others have noted the instability of amplicons >15 kb (Kwong, A. D. and Frenkel, N., *In Viral Vectors*, Eds. M. G, Kaplitt and A. D. Loewy, Academic Press: New York (1995), pp. 25–42), but this may be due to recombinogenic elements in the $ori_S$ or pac regions which could be mutated for increased stability. At least, theoretically, these amplicons could be increased in size up to 20 kb in plasmid constructs, 30–40 kb in cosmid constructs and 150 kb in large capacity cloning vectors. Shelling, A. N. and Smith, M. G., *Gene Ther.* 2:1–5 (1994) have shown that transgene cassettes flanked by the AAV ITRs in plasmids can integrate into human genomic DNA when delivered by co-transfection with rep. The inventors believe that a transgene cassette of at least 10 kb and possibly 20 kb, 30 kb, 40 kb, 50 kb or up to a maximum of 150 kb could be efficiently delivered within the HSV-AAV hybrid vector system of the present invention.

The hybrid vectors of the present invention can be generated using HSV-1 or AAV helper virus packaging systems well known in the art.

Amplicon vectors can now be generated free of helper virus using the helper virus-free packaging system described by Fraefel, C. et al, *J Virol.* 70: 7190–7197 (1996). To develop a helper virus-free packaging system, the DNA cleavage/packaging signals were deleted from a set of cosmids that represent the HSV-1 genome. Following cotransfection into cells, this modified cosmid set supported replication and packaging of vector DNA. Since the DNA cleavage/packaging signals were absent from the cosmid set, the HSV-1 genome is not packaged and consequently the vector stocks were free of detectable helper virus. The hybrid vectors of the present invention that have been generated in this helper virus free system are able to efficiently infect cells in culture, have more efficient gene transfer, more stable gene expression and have markedly reduced cytotoxic effects relative to vectors generated using helper virus systems.

Hybrid Vectors Mediate Stable Trangene Delivery and Expression

The experimental results set forth in the Examples indicate that the hybrid vectors of the present invention can mediate transgene expression for at least two weeks in actively dividing human glioblastoma cells in culture, considerably longer than traditional HSV amplicon vectors. Moreover, the transgene cassette is retained, and apparently amplified, over this period while the HSV amplicon sequences are lost within a week. When packaged in HSV virions in the absence of helper virus these hybrid vectors are essentially without toxicity and represent a "virtual" synthetic vector.

The state of the transgenes in the host cell nucleus is critical in determining the potential fidelity and extent of expression. Amplicon vectors deliver linear, double stranded DNA to the nucleus. If replication-competent HSV helper virus accompanies the amplicon DNA it commences replication as a rolling circle, but the cell will subsequently die within a day or so due to virus propagation. If, as in the present invention, the helper virus is replication-defective or absent, the amplicon DNA is thought to exist as a linear extrachromosomal element without any defined episomal structure. (See, FIG. 6) In non-dividing cells this DNA can be retained for extended periods, as determined by continued transgene expression for at least a month in neurons in vivo (e.g. During, M. J. et al., *Science* 266:1399–1403 (1994); Kaplitt, M. G. et al., *Mol. Cell. Neurosci.* 2:320–330 (1991)). However if the host cells are dividing, the amplicon sequences are lost within a few cell generations (Boothman, D. A. et al., *FEBS Lett.* 258:159–162 (1989); present study).

The features of the HSV-1 vectors incorporated into the hybrid vector of the present invention allow for limited replication (amplification) of the transgene cassette out from the amplicon DNA, increased episomal stability of ITR flanked transgene cassettes and potential integration into the host cell genome, as has been observed for HSV-1 vectors (McKeon, C. and Samulski, R. J., *Hum. Gene. Ther.* 7:1615–1619 (1996); Muzyczka, N., *Curr. Top. Microbiol. Immunol.* 158:97–129 (1992)). (See, FIG. 6)

While not wishing to be bound by theory, the inventors propose the following mechanism: the hybrid vector enters the host cell nucleus as a linear double stranded DNA concatenate. The transgene can be replicated out of the amplicon backbone thereby amplifying the transgene cassette and stabilizing it through hairpin hybridization of the AAV ITR sequences. Alternatively, it can integrate into the host cell genome. In the presence of Rep in human cells this should preferentially occur at the AAVS1 site on chromosome 19, but can also occur at random chromosomal sites in the presence or absence of Rep in different species.

Most HSV-1 vectors studied to date bear the transgene cassette flanked by the AAV ITRs with no rep gene. The DNA is delivered to the host cell nucleus in a single stranded form, probably with extensive secondary structure at either end ("hairpins"). The ITR sequences and cellular factors then mediate replication of the transgene cassette, and intermediates of this process include double stranded DNA forms with terminal "hairpin" configurations which resist nuclease digestion (Ward, P. and Bems, K. I., *J Virol.*

70:4495–4501 (1996)). Multiple copies of the transgene cassette can thus be generated and some fraction of these can integrate into the genome at random or specific sites (McKeon, C. and Samulski, R. J., Hum. Gene. Ther. 7:1615–1619 (1996)). Thus, transgene cassettes can be retained and expressed both in dividing cells and non-dividing cells for extended periods, with dividing cells being more permissive than non-dividing cells for these events (Russell, D. W. et al., Proc. Natl. Acad. Sci. USA 91:8915–8919 (1994)). The findings set forth inthe Examples are consistent with limited amplification of the transgene cassette following transduction with either the rep$^+$ or rep$^-$ hybrid vectors as noted by PCR amplification of the transgene cassette after two weeks in dividing cells and by the ability of the hybrid constructs to generate HSV-1 vectors following co-transfection with AAV rep-cap genes and a helper virus.

The rep gene of AAV encodes four isozymes, two of which 68 kd and 78 kd, are believed to have a major role in replication of AAV and integration into the site specific location on human chromosome 19q (Weitzman, M. D. et al., Proc. Natl. Acad. Sci. USA 91:5808–5812 (1994); Giraud, C. et al., Proc. Natl. Acad. Sci. USA 91:10039–10043 (1994)). The HSV/AAV hybrid vector incorporates the rep gene under its own promoter elements. Western blot analysis indicates that all isozymic forms are expressed by the vector. Although the Rep proteins can be toxic to cells, in the absence of helper virus they undergo feedback inhibition on their own promoter and thus their levels are expected to be reduced (Kyostio, S. R. M. et al., J Virol. 69:6787–6796 (1995)). There was no evidence of Rep-associated toxicity in the experiments set forth in the Examples. By placing it outside of the ITR-transgene-ITR cassette, the rep gene is predicted to be lost in dividing cells over a few cell divisions and should not be integrated into the host cell genome. Lack of integration should eliminate the rep gene as a potential source of toxicity and stabilize integrated transgene cassettes, as Rep also functions in excision of integrated AAV sequences from the genome (Bems, K. I., In Virology, pp. 2173–2197. Eds. B. N. Fields, D. M. Knipe and P. M. Howley. Lippincott-Raven, Philadelphia, Pa. (1996)). The percentage of cells expressing the transgene was always higher for rep$^+$ vectors as compared to rep$^-$ vectors, especially at later time points in the experiments set forth in the Examples. This could reflect more extensive replication and/or integration of the transgene cassette in the presence of Rep isozymes.

In summary, the Examples demonstrate that dividing U87 cells infected with the hybrid vectors of the present invention retained transgene expression longer than those infected with a conventional HSV amplicon vector, apparently through on site replication (amplification) of the ITR-flanked transgene cassette. The presence of the rep gene appeared to increase the stability of expression in this system, and packaging with the helper-virus-free system virtually eliminated toxicity. This vector has the potential to achieve stable transgene delivery to both dividing and non-dividing cells through amplification and/or chromosomal integration of the transgene cassette.

Gene Therapy Techniques

Gene therapy has been proposed as a method for treating disease states and genetic disorders that lack effective therapies. Gene therapy techniques can also be applied as a method to control expression of a protein and to assess its ability to modulate cellular events.

There are a number of inherited neurological and metabolic diseases in which defective genes are known and have been cloned. In some cases, the function of those cloned genes is known. For example, in humans, genes for defective enzymes have been identified for lysosomal storage disease, Lesch-Nyhan syndrome, amyloid polyneuropathy, Alzheimer amyloid, Duchenne's muscular dystrophy, for example. In addition, a number of other genetic diseases and disorders in which the gene associated with the disorder has been cloned or identified include diseases the of blood, such as, sickle-cell anemia, clotting disorders and thalassemias, cystic fibrosis, diabetes, disorders of the liver and lung, diseases associated with hormone deficiencies. Gene therapy could also be used to treat retinoblastoma, and various types of neoplastic cells which include tumors, neoplasms carcinomas, sarcomas, leukemias, lymphoma, and the like. Of particular interest are the central nervous system tumors. These include astrocytomas, oligodendrogliomas, meningiomas, neurofibromas, ependymomas, Schwannomas, neurofibrosarcomas, glioblastomas, etc.

Therapeutic Uses of the Hybrid Vectors

The HSV/AAV hybrid vectors of the present invention offer potential advantages over current vector systems for gene delivery to both dividing and non-dividing cells. In the Examples set forth below, human glioma cells were used as a model of brain tumors. In human glioblastomas in vivo, tumors consist of both dividing and non-dividing cells. It is important in gene therapy paradigms to deliver therapeutic genes to tumor cells in both states and to retain expression of sensitizing genes not only to tumor cells but also to the progeny of tumor cells which survive treatment. The hybrid vector system of the present invention, through amplification and/or integration into tumor cells, should be able to extend this therapeutic window in the context of gene delivery by HSV virions, which appear to be more infectious for these glioma cells than AAV vectors. These hybrid vectors of the present invention can be combined with recombinant HSV vectors to expand the therapeutic gene capacity of vectors and to allow on-site replication of vectors (Breakefield, X. O. et al., In The Internet Book of Gene Therapy: Cancer Gene Therapeutics, pp. 41–56 (1995); Hunter, W. et al., In Viral Vectors, Academic Press: New York (1995), pp. 259–274; Pechan, P. A. et al., Hum. Gene. Ther. 7:2003–2013 (1996)).

The hybrid vectors of the present invention have the combined delivery features of HSV virions, which have a large transgene capacity and can travel by retrograde transport from nerve terminals to the cell nucleus, and the stability features of AAV vectors, which include the capacity for amplification in the host cell nucleus and integration into the host genome. When packaged in helper-virus-free stocks these hybrid vectors are believed to provide a means of non-toxic, stable and efficient gene delivery to neurons.

The hybrid vector system of the present invention is, therefore, designed to provide a means of packaging plasmid DNA into highly infectious virions which can efficiently and safely deliver large transgenes to both mitotic and postmitotic cells in a state which can be maintained for extended periods.

The invention also provides for a hybrid vector wherein the inserted transgene sequence is a gene sequence associated with diseases and disorders. Non-limiting examples of such diseases and disorders include inherited metabolic disorders, including, lysosomal storage disease, Lesch-Nyhan syndrome, inherited neurological diseases, including, amyloid polyneuropathy, Alzheimer's Disease, Duchenne's muscular dystrophy, ALS, Parkinson's Disease, diseases of the blood, such as, sickle-cell anemia, clotting disorders and thalassemias, cystic fibrosis, diabetes, disorders of the liver and lung, heart and vascular disease, diseases associated with hormone deficiencies, movement disorders, pain, stroke, HIV, and cancer.

Thus, for disease and disorders listed above that are considered deficiency state diseases, gene therapy could be used to bring a normal gene into affected tissues for replacement therapy as well as to create animal models for the disease using antisense mutations. A deficiency state is "treated" by partially or wholly remedying the deficiency which is causes the deficiency or which makes it more severe.

For the treatment of cancers and tumors, gene therapy can be used to introduce a gene into the tumor cells that expresses a protein which is toxic or can trigger a toxic effect against tumor cells. Genes for transfer into the neoplastic cells by the hybrid vectors are selected from those which target host cell usually by expression of a gene product in the host neoplastic cells. "Gene product" broadly refers to proteins encoded by the particular gene. For the purposes of the invention, gene product also includes transcription products of the gene, particularly for use as antisense RNA. Genes are selected whose gene products serve to identify host cells, slow down or temporarily stimulate host cell growth in order to render the host cell more sensitive to chemotherapeutic agents and/or whose products target the host cell for cell death. Cell death can be accomplished by contacting the host cells, containing the gene product, with a subsequent treatment, either physical or chemical treatment. Alternatively, the gene products themselves may serve to kill the host cells or slow down cell growth. The host cells targeted by the present hybrid vectors are those cells into which the hybrid vector infects and expresses the desired gene product and thus can constitute neoplastic cells infected by the hybrid vectors.

Useful gene products comprise: tumor suppressor genes, which encode transcription factors which suppress cell growth, such as the Rb gene for retinoblastoma or the p53 gene in colon cancer (Huang et al., *Science* 242: 1563–1566 (1988); Barker, et al., *Science* 249: 912–915 (1980); toxic proteins that are released by cells, such as a fusion protein comprising a toxin coupled to EGF ligand (Heinbrook et al., *Proc. Natl. Acad. Sci. USA* 87: 4697 (1990)); products which themselves are capable of selective cell killing, such as anti-sense nucleic acid for essential cell proteins, such as replication proteins which serve to render the host cells incapable of further cell growth and division (Rosengberg et al., *Nature* 313: 703–706 (1985); Preiss et al., Nature 313:27–32 (1985) McGarry et al.,*Proc. Natl. Acad. Sci USA* 83: 399–403(1986); and prodrug activating genes such as thymidine kinase (Kramm et al., *Brain Pathology* 5:345–381 (1995)).

For example, a hybrid vector which incorporates the HSV-1 thymidine kinase gene offers such a conditional killing mechanism for dividing cells. The thymidine kinase enzyme can convert certain nucleoside analogues, such as, acyclovir, ganciclovir, and FIAU. These drugs are converted to nucleotide-like precursors and incorporated into the DNA of the replicating cells, thus disrupting the integrity of the genome and ultimately leading to cell death. (See, Boviatsis et al. *Cancer Res.* 54:5745–5751 (1994). Thus, the hybrid vector administered in combination with a less toxic drug could be highly effective treatment for tumors.

In addition, the hybrid vector can also incorporate the gene for cytochrome P450. The cytochrome P450 gene offers a conditional killing mechanism independent of the cell cycle of the tumor cell. This gene is used to sensitize neoplastic cells to the cytotoxic effects of a chemotherapeutic agent that is activated by one or more cytochrome P450 genes. The term cytochrome P450 gene, as used herein, means a mammalian cytochrome P450 gene such as, P450, 2B1, P450 2B6, P450 2A6, P450 2C8, P450 2C9, P450 2C11, or P4503A4. Each of these genes has been linked to activation of the anticancer drugs cyclophosphamide, oxazaphophorine or ifosphamide (Clarke et al., *Cancer Res.* 49:2344–2350(1989); Chang et al., *Cancer Res.* 53:5629–5637(1993); Weber et al., *Biochemical Pharmacology* 45:1685–1694 (1993), and the cDNA sequences of these genes have also been published (Nelson et al., *DNA and Cell Biology* 12:1–51 (1993) and references cited therein; Yamano et al., Biochem. 29:1322–1329 (1990); Yamano et al., *Biochem.* 28:7340–7348 (1989). Persons of ordinary skill in the art will be able to utilize the method of the present invention with numerous other anticancer drugs that are activated by members of the cytochrome P450 family of enzymes that are homologous to the aforementioned cytochromes.

In a preferred embodiment, the cytochrome P450 2B 1 gene is utilized to sensitize central nervous tumor cells to the cytotoxic effects of cyclophosphamide (CPA). Expression of cytochrome P450 2B1 gene in C6 glioma cells was found to lead to tumor cell destruction following CPA treatment in culture, in subcutaneous tumors in athymic mice, in MCF-7 human breast carcinoma cells and in experimental brain tumors in mice. The P450 2B1 gene has been successfully utilized to sensitize tumors cells such as 9L gliosarcoma cells to oxazaphosphorine treatment.

The hybrid vector can be administered to the tumors in a mammal by multiple routes, including direct injection into the tumor mass, through the blood vessels and via cerebrospinal fluid.

The gene product may also encode a chemical or protein which renders the host cells radiosensitive and thus more susceptible to killing by radiation. Thus, upon subsequent subjection to radiation, the host cells are selectively killed.

Thus, the following types of cancers and tumors can be treated using the present hybrid vectors for gene transfer include neoplastic cells which include tumors, neoplasms carcinomas, sarcomas, leukemias, lymphoma, and the like. Of particular interest are the central nervous system tumors which include astrocytomas, oligodendrogliomas, meningiomas, neurofibromas, ependymomas, Schwannomas, neurofibrosarcomas, glioblastomas, etc.

Thus, the invention further provides a method for expressing a transgene in a cell which comprises:
 (a) introducing a HSV/AAV hybrid vector into the cell; and
 (b) permitting the vector to express the transgene in the cell.

The invention also provides a method of selectively killing tumor cells comprising:
 (a) infecting said tumor cells with a hybrid vector expressing thymidine kinase comprising
  (i) a DNA sequence derived from Herpes Simplex Virus (HSV) comprising a HSV origin of DNA replication and packaging signal;
  (ii) inverted terminal repeat sequences from Adeno-Associated Virus (AAV) flanking a thymidine kinase transgene cassette; and
  (iii) an AAV rep gene inserted outside the inverted terminal repeat flanked transgene cassette
   wherein expression of the thymidine kinase gene product renders said tumor cells sensitive to a nucleoside analog;
 (b) administering an effective amount of a nucleoside analog; and (c) selectively killing said tumor cells.

The invention further provides for a method of selectively killing tumor cells comprising:

(a) infecting said tumor cells with a hybrid vector expressing cytochrome P450 comprising:
  (i) a DNA sequence derived from Herpes Simplex Virus (HSV) comprising a HSV origin of DNA replication and packaging signal;
  (ii) inverted terminal repeat sequences from Adeno-Associated Virus (AAV) flanking a cytochrome P450 transgene cassette;
  (iii) an AAV rep gene inserted outside the inverted terminal repeat flanked transgene cassette
    wherein expression of the cytochrome P450 gene product renders said tumor cells sensitive to a chemotherapeutic agent;
(b) administering to the patient an effective amount of a chemotherapeutic agent that is activated by the cytochrome P450 enzyme; and
(c) selectively killing said tumor cells.

The invention also provides a method of treating diseases and disorders such as inherited metabolic disorders, including, lysosomal storage disease, Lesch-Nyhan syndrome, inherited neurological diseases, including, amyloid polyneuropathy, Alzheimer's Disease, Duchenne's muscular dystrophy, ALS, Parkinson's Disease and brain tumors, diseases of the blood, such as, sickle-cell anemia, clotting disorders and thalassemias, cystic fibrosis, diabetes, disorders of the liver and lung, heart and vascular disease, diseases associated with hormone deficiencies, movement disorders, pain, stroke, and HIV, tumors, neoplasms, carcinomas, sarcomas, leukemias, lymphoma, astrocytomas, oligodendrogliomas, menigiomas, neurofibromas, ependymomas, Schwannomas, neurofibrosarcomas, and glioblastomas.

Having generally described the invention, the same will be more readily understood by reference to the following examples, which are provided by way of illustration and are not intended as limiting.

EXAMPLES

The hybrid vectors of the present invention were evaluated for their ability: 1) to express Rep isozymes; 2) to be packaged into both HSV-1 and AAV virions depending on the helper virus used; and 3) to confer transgene expression on dividing cells in culture. HSV-1 packaged vectors, with or without helper virus, were used to infect dividing U87 human glioma cells and marker (lacZ) gene expression and cell toxicity were evaluated over time comparing both rep$^+$ and rep$^-$ hybrid amplicon vectors and conventional amplicon vectors.

Materials and Methods

Cell Culture

The cell line, V27, was derived from Vero cells as a stable clone constitutively expressing the HSV-1 ICP27 gene (Rice, S. A. and Knipe, D. M., *J Virol.* 64:1704–1715 (1990); provided by Dr. David Knipe, Harvard Medical School). The 2.2 cell line, a similar Vero-derived clone expressing HSV-1 ICP 27, was provided by Dr. Sandri-Goldin (Univ. Calif. Irvine; Smith, I. L. et al., *Virol* 186:74–86 (1992)). Human kidney tumor line, 293, hamster kidney line, BBK, and human glioma line, U87, were obtained from the American Type Culture Collection (ATCC). All cells were propagated at 37° C. in a 5% $CO_2$-95% air atmosphere in either Dulbecco's Modified Eagle Medium (DMEM), or Minimal Essential Medium (293 cells only) (Mediatech, Washington, D.C.), containing 10% fetal bovine serum (FB S) (Hyclone, Logan, Utah), 100 U/ml penicillin, and 100 ug/ml streptomycin (Sigma).

Vector Constructs

Constructs used in the experiments are depicted in FIG. 1.

Generation and Titration of Vector Stocks

Amplicon Vectors

The generation of helper virus-positive amplicon vector stocks was initiated by transfection of V27 cells (1×10$^6$ per 25 cm flask) with 10 ug amplicon plasmid DNA by using Lipofectamine™ (Gibco/BRL, Gaithersburg, Md.) according to manufacturer's protocol. Twenty-four hrs later cells were infected with the HSV-1 mutant helper virus, d27-1, at a multiplicity of infection [MOI; plaque forming units (pfu) per cell] of 3. d27-1 has a 1.2 kb deletion within the ICP27 gene (Rice, S. A. and Knipe, D. M., *J Virol.* 64:1704–1715 (1990)). Cells were rinsed 2 hr post-infection and virus propagation was allowed to proceed for 48 hr until 90% cytopathic effect (CPE) was observed. To prepare vector stock, cells were harvested, frozen at 80° C. and thawed together with media three times, and cell debris was removed by centifugation. For virus stock passages P1 through P3, fresh V27 cells were infected by adding one quarter the amount of medium from the previous passage to the culture medium.

Helper-virus-free amplicon stocks were generated as described by Fraefel, C. et al., *J Virol.* 70:7190–7197(1996). Briefly, cosmids spanning the HSV-1 genome (Cunningham, C. and Davison, A. J., Virology 197:116–124 (1993)) and having deleted DNA cleavage/packaging sequences (Fraefel, C. et al., *J Virol.* 70:7190–7197 (1996)) were co-transfected with amplicon DNA into 2.2 cells using Lipofectamine. All vector stocks were stored at −80° C.

The HSV-1 helper virus was titered as pfu/ml by standard plaque assays on 90% confluent V27 cell monolayers (Johnson, P. A. and Friedmann, T., *Meth. Cell. Biol.* 43:211–230 (1994)). Plaques were counted 48 hrs post-infection. The amplicon vectors were titered as transducing units/ml by histochemical staining for bacterial β-galactosidase 24 hrs after infection of 293 cells. Following 4% paraformaldehyde fixation, the cells were washed with phosphate buffered saline, pH7.4 (PBS) and stained using the X-gal substrate (5-bromo-4-chloro-3-indolyl-B-D-galactosidase), as described (Price, J. et al., *Proc. Natl. Acad. Sci. USA* 84:156–160 (1987)). The number of β-galactosidase positive cells was counted using an inverted phase Nikon Diaphot microscope at 10× magnification.

Recombinant AAV (rAAV) stocks were prepared as described by Kaplitt, M. G. et al., *Nat. Genet.* 8:148–154 (1994). Briefly, 293 cells were split into 100 mm dishes, and grown overnight to approximately 70% confluence. Cells were then cotransfected with 4 μg of either pAB-11 or recombinant HSV/AAV amplicon constructs and 4 μg of the helper plasmid pAAV/Ad8, using Lipofectamine™. Since pAAV/Ad8 contains the adenovirus type 5 terminal sequences (107 bp) in place of the AAV ITRs, it cannot be packaged into AAV virions (Samulski, R. J. et al., *J Virol.* 63:3822–3825 (1989)). Six hours after transfection, the medium was removed and replaced with fresh medium. At 24 hr post-transfection, cells were infected with either adenovirus type 5 (d1309) (Jones, N. and Shenk, T., *Cell* 17:683–689 (1979)) at an MOI of 5, or with HSV-1 mutant d27-1 at a MOI of 10. At 48 hr post-infection, cells were collected and frozen-thawed three times to lyse the cells and release virions. Lysates were stored at −20° C.

rAAV titer (transducing units) were determined by X-gal histochemistry on 293 cells. Cells at 70–90% confluency grown on poly L-lysine coated coverslips, were rinsed with PBS, and incubated with lysate in a total volume of 0.25 ml for 30 min. Cells were then washed and incubated in medium supplemented with 2% fetal calf serum for about 30 hr, at which time they were stained for (β-galactosidase activity (as above).

Western Blot Analysis

The expression of AAV Rep proteins by pHS/AVrep$^+$ was evaluated by Western blotting using the hybridoma supernatant of the monoclonal antibody 1F11.8, which recognizes all four Rep isoforms. Two μg each of purified psub201(wild type AAV rep and cap sequences), pHS/AV rep$^+$, and pHS/AV rep$^-$ were transfected for 6 hr by using Lipofectamin™ into late log phase human 293 cells. After 48 hr, the cell monolayers were rinsed with PBS, and incubated on ice for 30 min in cell lysis buffer (50 mM Tris-Cl, pH 8.0, 150 mM NaCl, 0.02% NaAzide, PMSF, aprotinin, 0.1% SDS and 1% Triton X-100). Samples were diluted with 2× Laemmli loading buffer (Sambrook, J. et al., *In Molecular Cloning. A Laboratory Manual*, Cold Spring Harbor Laboratory Press: Cold Spring Harbor (1989)) and electrophoresed on denaturing 12.5% acrylamide gels. Proteins were transferred to Hybond-ECL membrane (Amersham, Arlington Hts., Ill.) by standard tank transfer in Tris-glycine-methanol transfer buffer at 100 V constant voltage (Fazakerley et al., *Virology* 167: 422–432 (1988)). Non-specific membrane binding was blocked by incubating the membrane for 1 hr incubation in 5% non-fat dry milk in PBS-Tween (Sambrook, J. et al., *In Molecular Cloning A Laboratory Manual*, Cold Spring Harbor Laboratory Press: Cold Spring Harbor (1989)). After washing with PBS-Tween, the membrane was incubated for 1 hr with 1F11.8 (1:1000 dilution in 1% nonfat dry milk/PBS-Tween). The membrane was washed and incubated with horseradish peroxidase-conjugated sheep anti-mouse immunoglobulin (1:2000 dilution in blocking solution) for 1 hr. The membrane was then washed and developed by using the ECL reagents (Amersham).

Time Course of LacZ Expression and Cell Viability in U87 Cells

Infection of duplicate wells of U87 cells (2×10$^5$ per 36 mm well) with virus stocks was carried out to achieve a constant MOI of amplicon vectors (0.05 transducing units per cell) with or without helper d27-1 virus, or comparable pfu/ml of helper virus. Stocks were diluted with media to the appropriate MOI in a total volume of 1.5 ml per well. Infection was carried out at 37° C. for 24 hr and then virus was removed and either fresh media was added (for later time points) or time point analysis was carried out as described below. At each time point—1, 2, 5, 10 and 15 days, the following procedures were carried out: 1) fixation and staining of cells for β-galactosidase activity (as described above); 2) trypsinization of monolayers for automated cell counts (Coulter Electronics Inc.), and viability assessment by trypan blue exclusion; and 3) harvesting of cellular DNA for PCR analysis. At days 5 and 10, cells were split 1:4 and carried to the next time point.

DNA Extraction and PCR

Genomic DNA was extracted from human U87 glioma cells which had been transduced with the hybrid amplicon vectors, HS/AV rep$^-$ and HS/AVrep$^+$, the control amplicon, Hermes-L, or rAAV AB-11 by using the QIA amp protocol (Qiagen, Chatsworth, Calif.). Control genomic DNA included mock transfected U87 cells and HSV-1 d27-1 infected U87 cells. Double stranded PCR reactions contained: 4 μl of genomic DNA in HPLC water, 10 ng of the appropriate primer, 1X PCR buffer (TaKaRa, Japan), 200 μl each of dGTP, dATP, dTTP and dCTP, and 1.25 units of Taq polymerase sealed with 200 μl mineral oil. The samples underwent an initial denaturation at 94° C. for 2 min, followed by 30 cycles of: 94° C. for 1 min, 55° C. for 1 min. 72° C. for 2 min. This reaction was completed by incubation at 72° C. for 10 min for final extension. Ten μl of each reaction were then electrophoresed on a 1.5% agarose gel. Primer pairs used for PCR include:

1) LacZ: 5'GCTTTCGCTACCTGGAGAGACGC3' (SEQ ID NO:1)
   5'ATCGCTATGACGGAACAGGTATTC3' (SEQ ID NO:2)
2) βActin amplimer set (CLONTECH, Palo Alto, Calif.)

Example 1

Preparation of HSV Vector Stocks

HSV amplicon vector stocks were titered as transducing units per ml on 293 cells for amplicons and as pfu per ml on V27 cells for helper virus. The following range of titers were obtained for different vectors HS/AVrep$^+$ stocks: amplicon, 1–6×10$^4$ transducing units/ml; helper virus 3×10$^4$–10$^8$ pfu/ml; HS/AVrep$^-$ stock: amplicon, 8×10$^4$ transducing units/ml; helper virus 7×10$^4$–10$^8$ pfu/ml; Hermes-L: amplicon 2×10$^5$ transducing units/ml; helper virus 8×10$^4$–7×10$^7$ pfu/ml. Titers of d27-1 helper virus grown alone on V27 cells were 3×10$^6$ pfu/ml. Titers of helper-free amplicon vectors were—HS/AV rep$^+$, 2×10$^4$ transducing units/ml; HS/AVrep-, 1×10$^5$ transducing units/ml; Hermes-L, 1×10$^5$ transducing units/ml. For all helper virus positive stocks the ratio of amplicon vector to helper virus was very low—1:10$^4$ for HS/AV rep$^+$, 1:10$^3$ for HSV/AV rep$^-$ and 1:300 for Hermes-L. The poorer packaging efficiency of HS/AV rep$^+$ <HSV/AV rep$^-$<Hermes control was consistent across stocks prepared on separate occasions, for both helper-positive and helper-free amplicon stocks.

Example 2

AAV Functions in the HSV/AAV Hybrid Vectors

Figure 2:
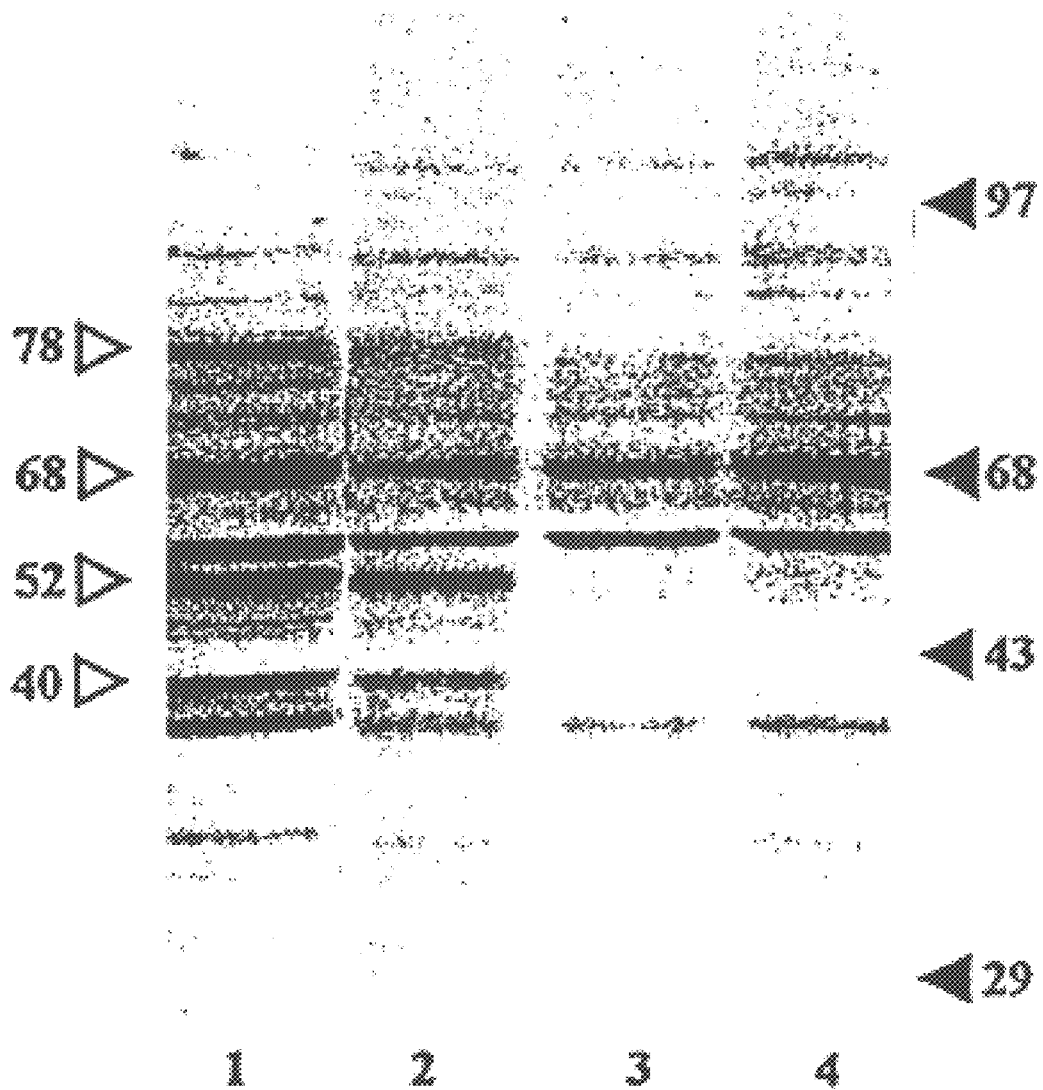
FIG. 2. Expression of Rep isozymes. Human 293 cells were transfected with the following plasmids: lane 1—psub201, encoding the wild type AAV genome, including rep and cap; lane 2—pHS/AVrep$^+$; lane 3—pHS/AVrep$^-$; or were (lane 4—) non-transfected. Cells were harvested after 24 hrs and proteins resolved by SDS PAGE and analyzed by Western blots using a 1:1000 dilution of monoclonal antibodies to Rep isozymes. Position of MW markers is shown on left; position of Rep isozymes on right.

Two properties of AAV were assessed using HS/AV amplicons: 1) expression of Rep isozymes and 2) the ability of the transgene cassette to be packaged into AAV virions. In order to evaluate expression of Rep isozymes, 293 cells were transfected with pHS/AV-Rep$^+$, pHS/AV-Rep$^-$, or psub201. Twenty-four hr after transfection cellular proteins were resolved by SDS-PAGE and analyzed on Western blots using a monoclonal antibody to Rep which recognizes all isoforms (FIG. 2). The presence of immunoreactive Rep proteins was specific to plasmids bearing the rep gene. Three isozymes, corresponded to Rep 40, 52 and 78, could be resolved and were present in cells transfected with psub201 and pHS/AVrep$^+$, and not in those transfected with pHS/AVrep$^-$ or non-transfected. (Rep 68 co-migrated with a non-specific cellular protein and thus could not be evaluated.)

The lacZ transgene cassette flanked by AAV ITRs in the hybrid plasmids, as well as in the control pAB-11 rAAV, was assessed for its ability to be packaged into AAV virions both by co-transfection with helper plasmid pAAV/Ad8 and infection with the adenovirus mutant, d1309 (Samulski, R. J. et al., *J. Virol.* 63:3822–3825 (1989)), or by co-transfection with pAAV/Ad8 and infection with the replication-defective HSV mutant, d27-1. The transgene cassette was able to be packaged into AAV vectors using either helper virus (Table 1). Titers of AAV vectors using the adenovirus helper were comparable for the HSV/AAV hybrid vectors and the AAV transgene construct, pPAB-11, 5–9×10$^4$ transducing units/ml. Titers of AAV vectors using HSV helper were 2-3-fold lower, 2–4×10$^4$ transducing units/ ml, but again similar for the hybrid and AAV vector constructs. The possibility that the transducing units represent hybrid constructs packaged in HSV-1 virions in the presence of d27-1 was excluded because d27-1 is replication-defective in the 293 cells used for generating AAV vector stocks and thus could not support generation of HSV-1 amplicon vectors.

TABLE 1

Packaging of Transgene Cassettes into AAV Virions

| Vector stock[a] | Adenovirus Helper | HSV Helper |
|---|---|---|
| | (transducing units/ml)[b] | |
| pHS/AVrep+ | $5 \times 10^4$ | $2 \times 10^4$ |
| pHS/AVrep- | $6 \times 10^4$ | $3 \times 10^4$ |
| pPAB11 control | $9 \times 10^4$ | $4 \times 10^4$ |

[a]Vector stocks were prepared by co-transfection of 293 cells with HSV/AAV amplicon constructs or pAB11 and helper plasmid pAAV/Ad8, followed by infection with replication-defective helper virus—either adenovirus type 5 dl309 or HSV-1 d27-1.
[b]Vector stocks were titered by transduction of 293 cells and staining for lacZ expression 24 hrs later.

Example 3
Gene Delivery
Helper Virus-positive HSV Amplicon Vectors

To assess the stability of transgene expression in dividing cells, actively proliferating U87 human glioma cells were infected with one of the two hybrid vectors, HS/AVrep+ or HS/AVrep-, or with the conventional amplicon vector, Hermes-L, or with d27-1 HSV helper virus alone. At subsequent time points, days 1, 2, 5, 10 and 15 post-infection, cells were assessed for transgene expression and viability. Amplicon vector stocks were kept constant with respect to the MOI of the amplicon vectors, 0.05 transducing units/cell, while the associated MOI of helper virus varied among stocks—500 pfu/cell for HS/AVrep+, 50 for HS/AVrep- and 15 for Hermes-L.

Amplicon vectors at MOI=0.05 (transducing units per cell as titered on 293 cells) resulted in an initial transduction efficiency of only about 0.05% in U87 cells (FIG. 3A), indicating that the vectors have a lower transduction efficiency on U87 as compared to 293 cells. Low amplicon vector MOI's were mandated by the rate limiting amounts of vector stock available and the toxicity of the helper virus. For the control Hermes-L amplicon vector, the number of β-galactosidase positive cells was highest (1%)24 hr after infection, and then decreased to 0.05% by day 2 and to 0.003% by day 5, with no positive cells noted on day 10. Transgene expression mediated by the HSV/AAV hybrid vectors was similar to the conventional amplicon vector on day 1 (about 1% of cells), but then remained on with 0.2–0.3% positive cells remained on day 5 (100× more than the conventional amplicon vectors) and 0.02–0.1% positive on day 10. On day 15 the proportion of cells expressing the transgene was notably higher for cells transduced with the HS/AV rep+ vector (0.05%) as compared to those transduced with the HS/AV rep- vector (<0.001%), indicating that expression of Rep isozymes promoted retention and sustained expression of the transgene up to 2 weeks.

Cell viability was also assessed over-time in order to determine the toxicity of the helper virus positive vector stocks. Comparisons were carried out among uninfected U87 cells, cells infected with HSV helper virus alone (d27-1), or helper virus-positive rep+ or rep- amplicon vectors (FIG. 3B). Viability dropped markedly by day 2 for both d27-1 (MOI 16 pfu/cell) and HS/AV rep+ vector (d27-1 MOI=500), with a maximum loss of viable cells 6 days after infection with HS/AV rep+, however, transduced cell populations resuming log growth by day 11. Stocks of the Hermes-L amplicon control vector (d27-1 MOI=40) and HS/AV rep-(d27-1 MOI=55) caused an apparent temporary growth arrest for 6–11 days after infection and then cells resumed growth at a rate similar to uninfected U87 cells. These results indicated that the helper virus caused substantial toxicity to cells.

Helper Virus-negative HSV Amplicon Vectors

To resolve whether cell toxicity was due solely to the helper virus or also to expression of Rep isozymes by the rep+ hybrid vector, parallel experiments were carried out using the hybrid and control amplicon vectors generated using a helper-virus-free system at an MOI of 0.05. The apparent transduction efficiency of U87 cells after 24 hours was 2-10-fold lower as compared to transduction using the same MOI of amplicon vectors in helper virus-positive stocks (FIG. 4A). This apparent decrease in transduction efficiency could be explained in two ways: 1) by a role for the helper-virus in the transduction process itself, e.g. by promoting nuclear replication of transgene cassettes; or 2) by the toxicity of the helper-virus, such that cells infected with helper virus have a reduced survival rate, while those infected with amplicon vectors have a good survival rate, so that the 1% positive cells in helper-positive stocks would be elevated by virtue of death of some negative cells. A time-dependent decrease in transgene expression was observed with all three different amplicon vectors. However, both HSV/AAV hybrid vectors conferred transgene expression in 0.003–0.008% of cells at 10 days, while no positive cells were observed for the Hermes-L vector at that time point. Again at the 15 day time point, cells infected with the rep+ vector still showed positive cells, while those infected with the rep- vector were negative. In fact, the HS/AV rep+ vector consistently showed a higher percentage of positive cells as compared to the HS/AV rep- vector at all time points. In this helper-virus-free system differences in the length of transgene expression cannot be explained by varying MOI of helper virus. Remarkably in this helper-virus-free system there was essentially no toxicity to U87 cells (FIG. 4B), and cell growth was comparable for uninfected cells (FIG. 3B) and cells infected with all three vectors over the two week post transduction period.

Example 4
State of Vectors in Transduced Cells

PCR analysis was carried out on total cellular DNA at various time points after infection of U87 with vectors using the helper-virus-free amplicon vector stocks. Two sets of primer pairs were used, one set specific to the lacZ transgene and one specific to the P-actin gene, as a control for cellular DNA. lacZ sequences were present at similar concentrations in cells infected with the control Hermes-L amplicon vector and the hybrid vectors at 1 and 5 days post-transduction. However by day 10 lacZ sequences were dramatically reduced in cells infected with the control and rep- vectors, while still abundant in cells infected with the rep+ vector. By day 15 the transgene sequences were virtually gone from cells infected with the Hermes-L vector and still present in cells transduced with the hybrid vectors, with rep+-infected cells having apparently more transgene sequences per cell population than rep+-infected cells.

CONCLUSION

The novel hybrid vectors of the present invention, which incorporate critical elements of both HSV amplicon vectors and AAV vectors, are able to sustain transgene expression in dividing glioma cells for over two weeks. These vectors combine the high infectibility and large transgene capacity of HSV vectors with the potential for episomal amplification and chromosomal integration of AAV vectors. The hybrid vectors contain the HSV-1 origin of DNA replication, oris, and the DNA cleavage/packaging signal, pac, which allow amplicon replication and packaging in HSV virions. The lacZ reporter gene under control of the CMV IEI promoter is flanked by AAV ITR sequences, which facilitate replication and genomic integration of this cassette in the host cell nucleus. Constructs were generated with or without the AAV rep gene (rep$^+$ and rep$^-$) to assess its importance in extending transgene expression. Expression of Rep isozymes was confirmed by western blot analysis. An HSV amplicon construct containing the reporter gene, but no AAV sequences, was used as a control. Constructs were packaged into HSV virions with or without helper virus and these vector stocks were used to infect human U87 glioma cells in culture. The hybrid vectors supported transgene retention and expression for 2–3 weeks, while the control amplicon vector lost the transgene after 10 days. Expression was somewhat longer for the rep$^+$ as compared to the rep$^-$ hybrid vectors. Toxicity due to the HSV helper virus was eliminated using helper-virus-free amplicon vector stocks. Hybrid vectors could also be packaged in AAV virions, using AAV and adenovirus helper functions. These HSV/AAV hybrid vectors are expected to allow long term, non-toxic gene delivery of DNA constructs to both dividing and non-dividing cells.

Example 5

Expression and Integration of the HSV/AAV Hybrid Vector

Expression of the Transgene in Human Immortalized cell lines:

In dividing HeLa and 293 cell (human immortalized cell lines) the inventors have demonstrated stable long term expression of an introduced transgene for long periods of time. Dividing cells were infected with equal amounts (multiplicity of infection=1) of both hybrid vector and traditional HSV-1 amplicon vector. Cells were split 1:5 every 4 days and the proportion of cells expression a flourescent transgene was measured by quantitative analysis on a flouresence activated cell sorter (FACS). The amplicon vector initially transduced >85% of total cells, but this expression decayed rapidly and remained less than 3% after 12 days in culture. In contrast, the hybrid vector was equally efficient at transducing cells, but supported transgene expression for 30 days in 40% of total dividing cells.

Integration of Transgene Sequences

Integration of transgene sequences into target cells is a design feature of the hybrid HSV/AAV vector. In a number of dividing human cell lines the inventors compared integration mediated by the hybrid vector to amplicon vectors. HeLa cells were infected with these vectors using methods well known to those skilled in the art and fluorescent cells were sorted as single cells into individual wells of a 96-well tissue culture plate. These clones were cultivated and at time points two and four weeks after transduction, integration was assessed by the presence of transgene sequences in genomic Southern blots. Approximately 30% of clones transduced with the hybrid vector contained a transgene copy, in agreement with the above population data. The amplicon vector controls had no transgene present (10 clones tested). The clones in which integration mediated by the hybrid amplicon was demonstrated were further characterized. Expression of the fluorescent transgene was stable over long periods in these clones in comparison to clones in which no integration occured. The clones are stable over time, expressing the transgene after >20 passages in culture. Transduction of cells with hybrid vectors having transgenes containing the NeoR gene has allowed selection of stable integration events with G418. Thus, in dividing cells analyzed at the population and clonal level, the hybrid vector of the present invention, in comparison to the amplicon controls, efficiently mediates integration in dividing human cells. Transgene expression over long periods is greatly enhanced by stable transduction with the hybrid vector of the present invention.

Expression and Integration of the Transgene in Neuronal Cells

Comparative studies of the hybrid vector of the present invention with AAV, adenovirus (Ad) and amplicon vectors in primary rat neuronal cultures have demonstrated nontoxic gene delivery, high proportion of transduction and stable expression. Neurons are relatively difficult to transfect by established means and one of the potential applications of the hybrid vectors of the present invention is gene delivery to the central nervous system (CNS).

The inventors have performed studies comparing the delivery and expression of transgenes delivered to rat neuronal cultures. Pure neurons (>90%) are isolated from the striatum and ventral mesencephalon of the rat brain. Equal multiplicities (MOI=1) of AAV, Ad and HSV amplicon vectors and the HSV/AAV hybrid vector of the present invention were added to each culture. At day 2, HSV-based vectors (amplicon and hybrid vector) directed transgene expression in 35% of striatal neurons and 20% of mesencephlic neurons respectively. Both AAV and Ad vectors transduced <10% of cultures transduced by the hybrid vector of the present invention (i.e., 10% in striatal cultures, 5% in mesencephalic cultures). Thus, HSV-derived vectors were the most efficient at transducing primary rat neurons, and the hybrid vector was able to direct transgene expression for the length of the culture. Vector associated cytotoxic effects were analyzed by cell morphology and induction of apoptic changes in the nuclear chromatin. Virtually no cytotoxicity was noted in the hybrid vector cultures, amplicon cultures, and AAV. Ad vectors were, however, mildly cytotoxic to neurons in this system.

For the experiments described above, the hybrid amplicon vector is packaged to high titers by the helper virus free system described by Fraefel et al. (J. Virol., 1996, supra). Vector packaged in this system is virtually devoid of cytotoxic effects.

It will be clear that the invention may be practiced otherwise than as particularly described in the foregoing description and examples.

The invention is susceptible to modifications and variations apparent to the reader skilled in the art. In particular, the present disclosure extends to combinations and subcombination of the features mentioned and disclosed herein.

The entire disclosure of all publications (including patents, patent applications, journal articles, laboratory manuals, books, or other documents) cited herein are hereby incorporated by reference.

What is claimed is:

1. A hybrid gene vector for expressing a polynucleotide sequence of interest, comprising,
   (i) a polynucleotide sequence of interest in operable linkage with a promoter;
   (ii) a subset of viral polynucleotide sequences from a herpesvirus comprising a herpesviral origin of replication and packaging signal sufficient for replication and packaging of the vector in herpesviral virions, and;
   (iii) a subset of viral polynucleotide sequences from an adeno-associated virus (AAV) comprising AAV elements sufficient to increase persistence of the vector in mitotic and non-mitotic cells;

wherein said polynucleotide sequences are in operable association for expressing said polynucleotide sequence of interest.

2. The hybrid gene vector of claim 1 further comprising an adeno-associated viral gene(s) and a suitable arrangement of AAV polynucleotide elements sufficient for replication and chromosomal integration of said polynucleotide sequence of interest into a cell.

3. The hybrid gene vector of claim 1, wherein said polynucleotide sequence of interest is arranged between AAV inverted terminal repeats (ITR), and wherein said hybrid gene vector includes an adeno-associated viral gene encoding a Rep enzyme which mediates replication and chromosomal integration of ITR-flanked polynucleotide sequences.

4. The hybrid gene vector of claim 1 wherein said AAV elements are suitably arranged for and sufficient to enable replication and packaging of the vector into AAV virions.

5. A hybrid vector for expressing a transgene comprising,
(a) a DNA sequence derived from a Herpes Simplex Virus (HSV) comprising a HSV origin of DNA replication and packaging signal; and
(b) inverted terminal repeat sequences from Adeno-Associated Virus (AAV) flanking a transgene cassette, wherein said transgene cassette comprises a polynucleotide sequence of interest operably linked to a promoter;

wherein said sequences are in operable association for expressing said transgene.

6. A hybrid vector for expressing a transgene comprising,
(a) a DNA sequence derived from a Herpes Simplex Virus (HSV) comprising a HSV origin of DNA replication and packaging signal;
(b) inverted terminal repeat sequences from Adeno-Associated Virus (AAV) flanking a transgene cassette, wherein said transgene cassette comprises a polynucleotide sequence of interest operably linked to a promoter; and
(c) an AAV rep gene inserted outside the inverted terminal repeat flanked transgene cassette;

wherein said sequences are in operable association for expressing said transgene.

7. A method for expressing a transgene in a cell in vitro, which comprises the step of introducing the hybrid vector of claim 5 into the cell, wherein said transgene is expressed at detectable levels in said cell.

8. The method of claim 7 wherein said cell is a non-mitotic cell.

9. A method for expressing a transgene in a cell in vitro, which comprises the step of introducing the hybrid vector of claim 6 into the cell, wherein said transgene is expressed at detectable levels in said cell.

10. The method of claim 9 wherein said cell is a non-mitotic cell.

* * * * *